(12) United States Patent
Rudolph et al.

(10) Patent No.: US 10,519,415 B2
(45) Date of Patent: Dec. 31, 2019

(54) ATTACHMENT DEVICE FOR SINGLE USE CONTAINERS

(71) Applicant: ABEC, Inc., Bethlehem, PA (US)

(72) Inventors: Eric Rudolph, Bethlehem, PA (US);
Pete Silverberg, Bethlehem, PA (US);
Candice Kofsky, Bethlehem, PA (US);
Paul Kubera, Bethlehem, PA (US);
Barry Reiss, Bethlehem, PA (US)

(73) Assignee: ABEC, INC., Bethlehem, PA (US)

( * ) Notice: Subject to any disclaimer, the term of this patent is extended or adjusted under 35 U.S.C. 154(b) by 531 days.

(21) Appl. No.: 15/035,709

(22) PCT Filed: Dec. 9, 2014

(86) PCT No.: PCT/US2014/069320
§ 371 (c)(1),
(2) Date: May 10, 2016

(87) PCT Pub. No.: WO2015/089056
PCT Pub. Date: Jun. 18, 2015

(65) Prior Publication Data
US 2016/0272931 A1 Sep. 22, 2016

Related U.S. Application Data

(60) Provisional application No. 61/913,960, filed on Dec. 10, 2013, provisional application No. 62/054,557, filed on Sep. 24, 2014.

(51) Int. Cl.
*C12M 1/12* (2006.01)
*G01M 3/32* (2006.01)
(Continued)

(52) U.S. Cl.
CPC ............... *C12M 37/02* (2013.01); *B65B 3/04* (2013.01); *B65B 55/00* (2013.01);
(Continued)

(58) Field of Classification Search
None
See application file for complete search history.

(56) References Cited

U.S. PATENT DOCUMENTS

| 131,875 A | 10/1872 | Hall et al. |
| 609,595 A | 8/1898 | Sprecher et al. |
| (Continued) |

FOREIGN PATENT DOCUMENTS

| DE | 3340353 A1 | 5/1985 |
| EP | 1172138 B1 | 7/2005 |
| (Continued) |

OTHER PUBLICATIONS

ASTM International—Designation No. F2391-05, ASTM F2391-05(2011) Standard Test Method for Measuring Package and Seal Integrity Using Helium as the Tracer Gas Current edition approved Apr. 1, 2005. Published May 2005 Copyright © ASTM International, 100 Barr Harbor Drive, PO Box C700, West Conshohocken, PA, 19428-2959 USA.

(Continued)

*Primary Examiner* — Nathaniel T Woodward
(74) *Attorney, Agent, or Firm* — Patrick J. Halloran

(57) ABSTRACT

This disclosure relates to equipment utilized to manufacture chemical agents, particularly biopharmaceuticals, using Disposable Containers (DCs).

6 Claims, 36 Drawing Sheets

(51) Int. Cl.
  *B65B 3/04* (2006.01)
  *B65B 55/00* (2006.01)
  *B65D 21/02* (2006.01)
  *C12M 1/00* (2006.01)

(52) U.S. Cl.
  CPC ......... *B65D 21/0233* (2013.01); *C12M 23/28* (2013.01); *C12M 37/04* (2013.01); *G01M 3/3209* (2013.01)

(56) References Cited

U.S. PATENT DOCUMENTS

| | | |
|---|---|---|
| 2,162,400 A | 6/1939 | Heath |
| 2,973,944 A | 3/1961 | Augustus |
| 3,177,932 A | 4/1965 | Smith, Jr. et al. |
| 3,373,802 A | 3/1968 | Wiklund et al. |
| 3,380,513 A | 4/1968 | Staats, Jr. et al. |
| 3,400,051 A | 9/1968 | Hofschneider |
| 3,604,690 A | 9/1971 | Traelnes |
| 3,662,817 A | 5/1972 | Kendrick et al. |
| 3,762,212 A | 10/1973 | Morley et al. |
| 3,776,042 A | 12/1973 | Werra et al. |
| 3,779,082 A | 12/1973 | Galloway |
| 3,978,918 A | 9/1976 | Nagatomo et al. |
| 3,986,934 A | 10/1976 | Muller |
| 4,029,143 A | 6/1977 | Goebel |
| 4,207,180 A | 6/1980 | Chang |
| 4,212,950 A | 7/1980 | Adams |
| 4,426,959 A | 1/1984 | McCurley |
| 4,460,278 A | 7/1984 | Matsubara et al. |
| 4,588,024 A | 5/1986 | Murray et al. |
| 4,588,085 A | 5/1986 | Sussman |
| 4,670,397 A | 6/1987 | Wegner et al. |
| 4,847,203 A | 7/1989 | Smart |
| 4,919,906 A | 4/1990 | Barber |
| 4,932,533 A | 6/1990 | Collier |
| 4,941,531 A | 7/1990 | Moiseeff |
| 4,985,208 A | 1/1991 | Sugawara et al. |
| 4,995,945 A | 2/1991 | Craig |
| 5,174,928 A | 12/1992 | Cheng et al. |
| 5,220,535 A | 6/1993 | Brigham et al. |
| 5,309,750 A | 5/1994 | Riley |
| 5,513,516 A | 5/1996 | Stauffer |
| 5,525,512 A | 6/1996 | Pieler et al. |
| 5,547,329 A | 8/1996 | Hirai et al. |
| 5,599,507 A | 2/1997 | Shaw et al. |
| 5,728,929 A | 3/1998 | Gevaud |
| 5,762,887 A | 6/1998 | Girod et al. |
| 5,907,093 A | 5/1999 | Lehmann et al. |
| 5,985,347 A | 11/1999 | Ejnik |
| 5,989,500 A | 11/1999 | Peacock et al. |
| 6,254,143 B1 | 7/2001 | Billmyer et al. |
| 6,264,360 B1* | 7/2001 | Lehmusvaara ..... B01F 15/0048 266/262 |
| 6,460,405 B1 | 10/2002 | Mayer et al. |
| 6,557,255 B2 | 5/2003 | Billmyer et al. |
| 6,664,095 B1 | 12/2003 | Suryanarayan et al. |
| 6,955,793 B1 | 10/2005 | Arencibia, Jr. |
| 7,231,811 B2 | 6/2007 | Sagi et al. |
| 7,308,819 B2 | 12/2007 | Kamio et al. |
| 7,373,944 B2 | 1/2008 | Lehmann |
| 7,384,783 B2 | 6/2008 | Baxter |
| 7,565,828 B2 | 7/2009 | Barcan et al. |
| 7,682,067 B2 | 3/2010 | West et al. |
| 7,682,823 B1 | 3/2010 | Runyan et al. |
| 7,815,851 B1 | 10/2010 | Lewis et al. |
| 8,282,267 B2 | 10/2012 | Castillo et al. |
| 8,381,780 B2 | 2/2013 | Fisher et al. |
| 8,534,120 B1 | 9/2013 | Pavlik |
| 8,658,419 B2 | 2/2014 | Knight |
| 9,228,165 B2 | 1/2016 | Knight et al. |
| 2002/0105856 A1 | 8/2002 | Terentiev et al. |
| 2003/0209344 A1 | 11/2003 | Fang et al. |
| 2003/0219453 A1 | 11/2003 | Maisonneuve et al. |
| 2004/0154331 A1 | 8/2004 | Horiuchi et al. |
| 2004/0190372 A1* | 9/2004 | Goodwin ............ B01F 13/0818 366/273 |
| 2005/0087434 A1* | 4/2005 | Tarancon ............... B01J 19/123 204/157.3 |
| 2005/0239198 A1* | 10/2005 | Kunas ..................... B01F 7/001 435/297.1 |
| 2005/0247110 A1 | 11/2005 | Sagi et al. |
| 2005/0272146 A1 | 12/2005 | Hodge et al. |
| 2006/0137742 A1 | 6/2006 | Smith et al. |
| 2006/0201662 A1 | 9/2006 | Gelbert et al. |
| 2006/0277975 A1 | 12/2006 | Barcan |
| 2006/0280028 A1* | 12/2006 | West ....................... B01F 7/001 366/331 |
| 2007/0096611 A1 | 5/2007 | Antonijevic et al. |
| 2007/0169916 A1 | 7/2007 | Wand et al. |
| 2008/0139865 A1 | 6/2008 | Galliher et al. |
| 2008/0145924 A1 | 6/2008 | Kobiyashi et al. |
| 2008/0206847 A1 | 8/2008 | Kunis et al. |
| 2009/0111179 A1 | 4/2009 | Hata et al. |
| 2009/0145591 A1 | 6/2009 | Rericha et al. |
| 2009/0180933 A1 | 7/2009 | Kauling et al. |
| 2009/0290962 A1 | 11/2009 | Fisher et al. |
| 2010/0062522 A1 | 3/2010 | Fanning et al. |
| 2010/0149908 A1 | 6/2010 | Singh et al. |
| 2010/0301042 A1 | 12/2010 | Kahlert |
| 2010/0303682 A1 | 12/2010 | Rizzi et al. |
| 2010/0326172 A1 | 12/2010 | Voute et al. |
| 2011/0011164 A1 | 1/2011 | Terentiev et al. |
| 2011/0013474 A1* | 1/2011 | Ludwig ............... B01F 3/04269 366/102 |
| 2011/0059523 A1 | 3/2011 | Knight |
| 2011/0188928 A1* | 8/2011 | West ....................... B23P 11/00 403/291 |
| 2012/0011867 A1 | 1/2012 | Koons et al. |
| 2012/0100605 A1 | 4/2012 | Kauling et al. |
| 2012/0218855 A1 | 8/2012 | Kunis et al. |
| 2013/0081995 A1* | 4/2013 | Larsen ................... C12M 29/04 210/443 |
| 2013/0171616 A1 | 7/2013 | Niazi |
| 2014/0349385 A1* | 11/2014 | Erdenberger ..... B01F 15/00714 435/302.1 |
| 2014/0366969 A1* | 12/2014 | Chaussin ............... C12M 29/00 137/590 |

FOREIGN PATENT DOCUMENTS

| | | |
|---|---|---|
| EP | 1616938 A2 | 1/2006 |
| EP | 1854871 A1 | 11/2007 |
| JP | 57125202 A2 | 8/1982 |
| JP | 6011408 A | 1/1994 |
| JP | 8082568 A | 3/1996 |
| WO | 9405991 A1 | 3/1994 |
| WO | 2008040568 A1 | 4/2008 |

OTHER PUBLICATIONS

Mccrea, et al., "Separation of Vaccinia Hemagglutinin from Infectious Virus Particles by Chromatography on DEAE Columns," Department of Biophysics, Yale University, 3 pgs, 1958.

Miyako, Yasuhiro et al, Helium Leak Test for Sterility Assurance of a Sealed Bag. I: Relationship of Helium Leak and Pinhole Diameter, PDA Journal of Pharmaceutical Science and Technology, Jul./Aug. 2002, pp. 183-191, vol. 56, No. 4, Osaka, Japan.

Miyako, Yasuhiro et al, Helium Leak Test for Sterility Assurance of a Sealed bag. II: Establishing a Test Method for the Manufacturing Process. DA Journal of Pharmaceutical Science and Technology, May/Jun. 2003, pp. 186-197, vol. 57, No. 3, Osaka, Japan.

Pethe et al. "Helium Integrity Testing—A New Way to Ensure Single-Use Bag Integrity," PharmPro.com, 2 pgs, 2011.

Seal Strength and Package Integrity—The Basics of Medical Package Testing Stephen Franks © TM Electronics, Inc. 10 Pages.

Standard Test Method for Pressure Decay Leak Test for Flexible Packages With and Without Restraining Plates Copyright © ASTM International 100 Barr Harbor Drive, PO Box C700, West Conshohocken, PA 19428-2959, United States Designation: F2095-07 e1.

(56) References Cited

OTHER PUBLICATIONS

TRANTER, Inc., Brochure—PlateCoil Heat Exchangers, Document PCC-5, 20 pgs, 2006.
UK P & I Club, Miller, T. "Carefully to Carry—Flexitanks", Report on Flexitanks and Their Use, 7 Pages.

* cited by examiner

SUC Assembly Packaging & Integrity Test

This assembly is intended to: (1) provide secure shipping of a disposable assembly (2) Allowing air to be added while maintaining sterility to integrity of the bag by providing structural support to allow overpressure with air.

Attach Pipe to lower Flange and prepare to attach tubing from filter to top flange.
Secure Filter in holder in top flange and cover to ensure that no sharp edges impinge as bag is inflated. This will need to be addressed with other port and connections to bag

Integrity Test of Bag

Add Air Through Filter via ¼ " pipe nipple, pressurize to 5 psi...hold pressure X time note Pressure drop < X, then bag is integral. This is a significantly more sensitive than current IT tests and can be done during installation. Additionally, air flow from Air out can be measured by inverted cylandar in water

FIGURE 7
A.
Deployment of the SUC.
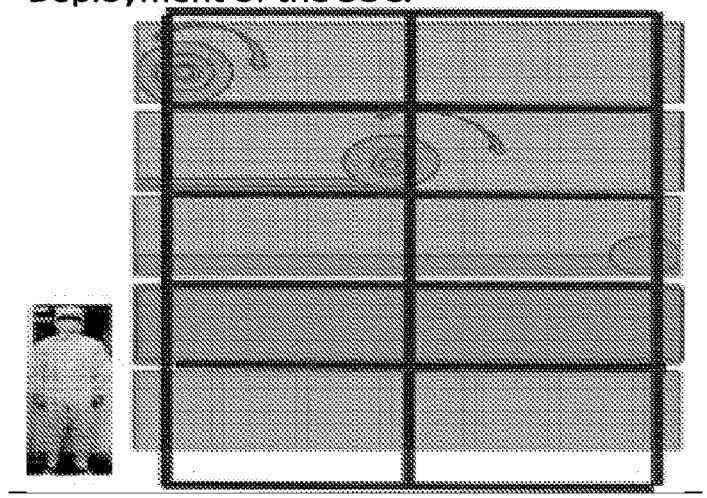
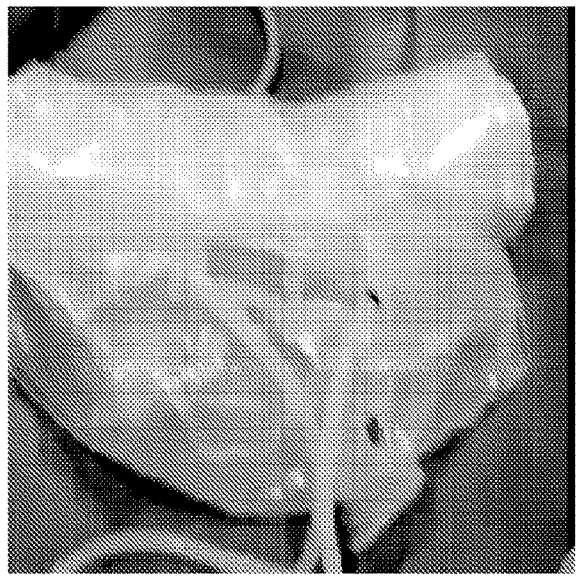

- Mesh to retain plastic granules used to break foam
- Tubing to provide container for plastic granules
- plastic granules used to break foam

- Mesh to retain plastic granules used to break foam
- Tubing to provide container for plastic granules
- plastic granules used to break foam 1. Shaft
2. Static seal face
3. Rotating Seal Face
4. Seal Spring
5. Bearing
6. Seal Housing
7. Seal Housing Cover
8. Retaining Screw

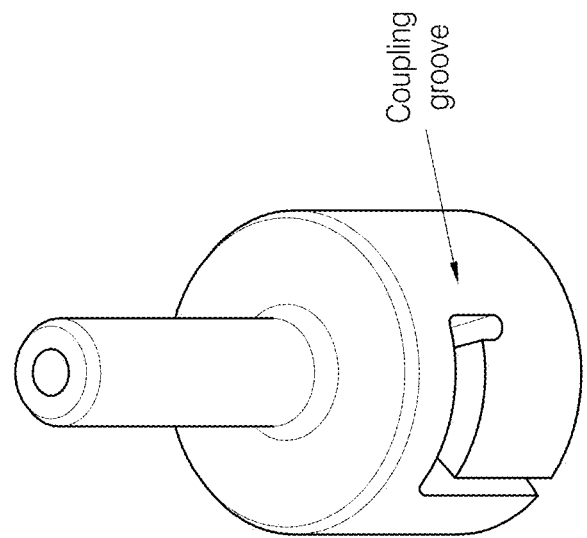
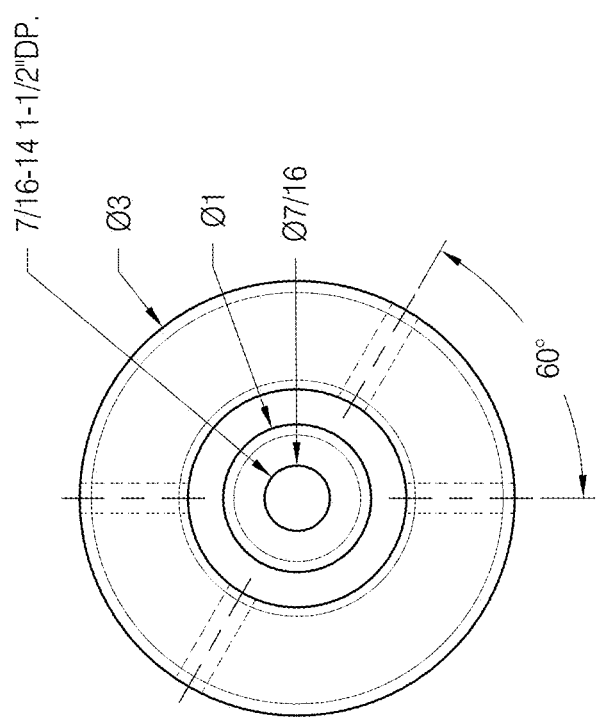
FIG. 10A

A. Baseline  B. Yo Yo  C. Gusset

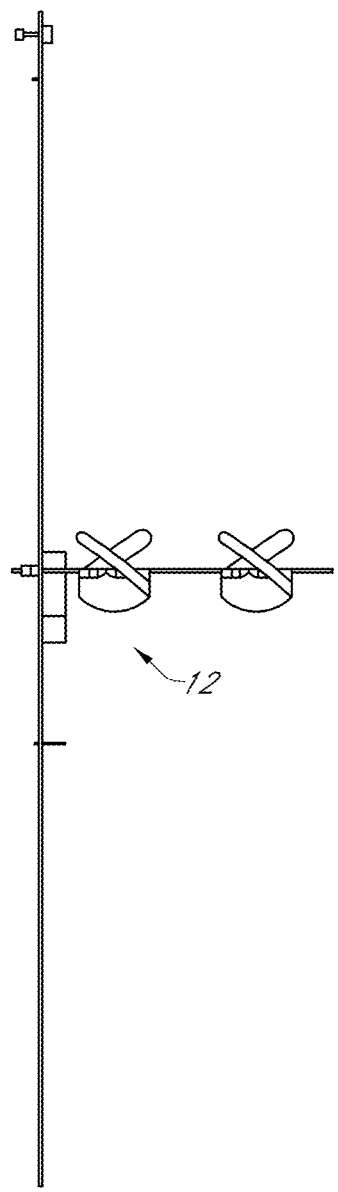
FIG. 14A1

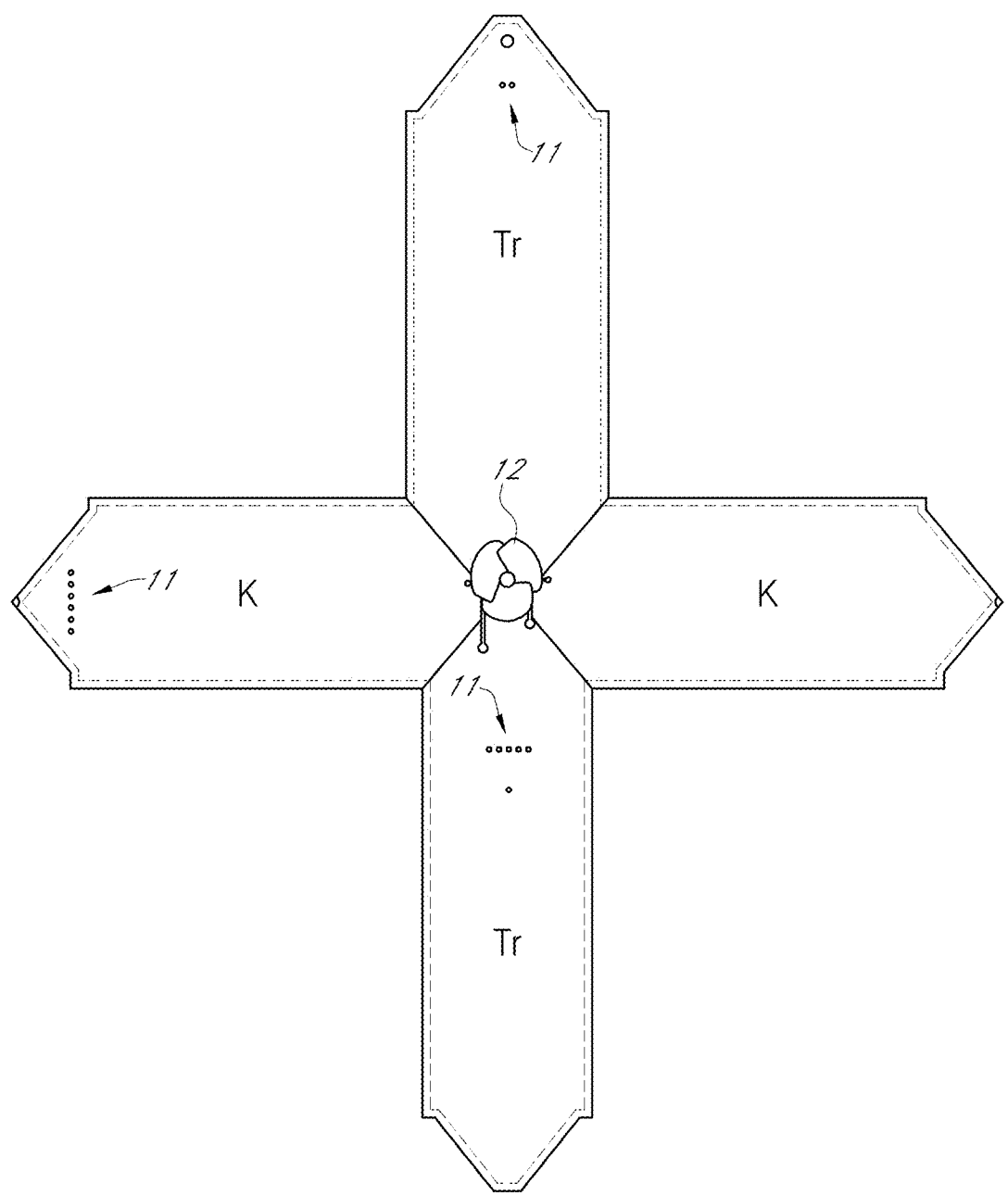
FIG. 14A2

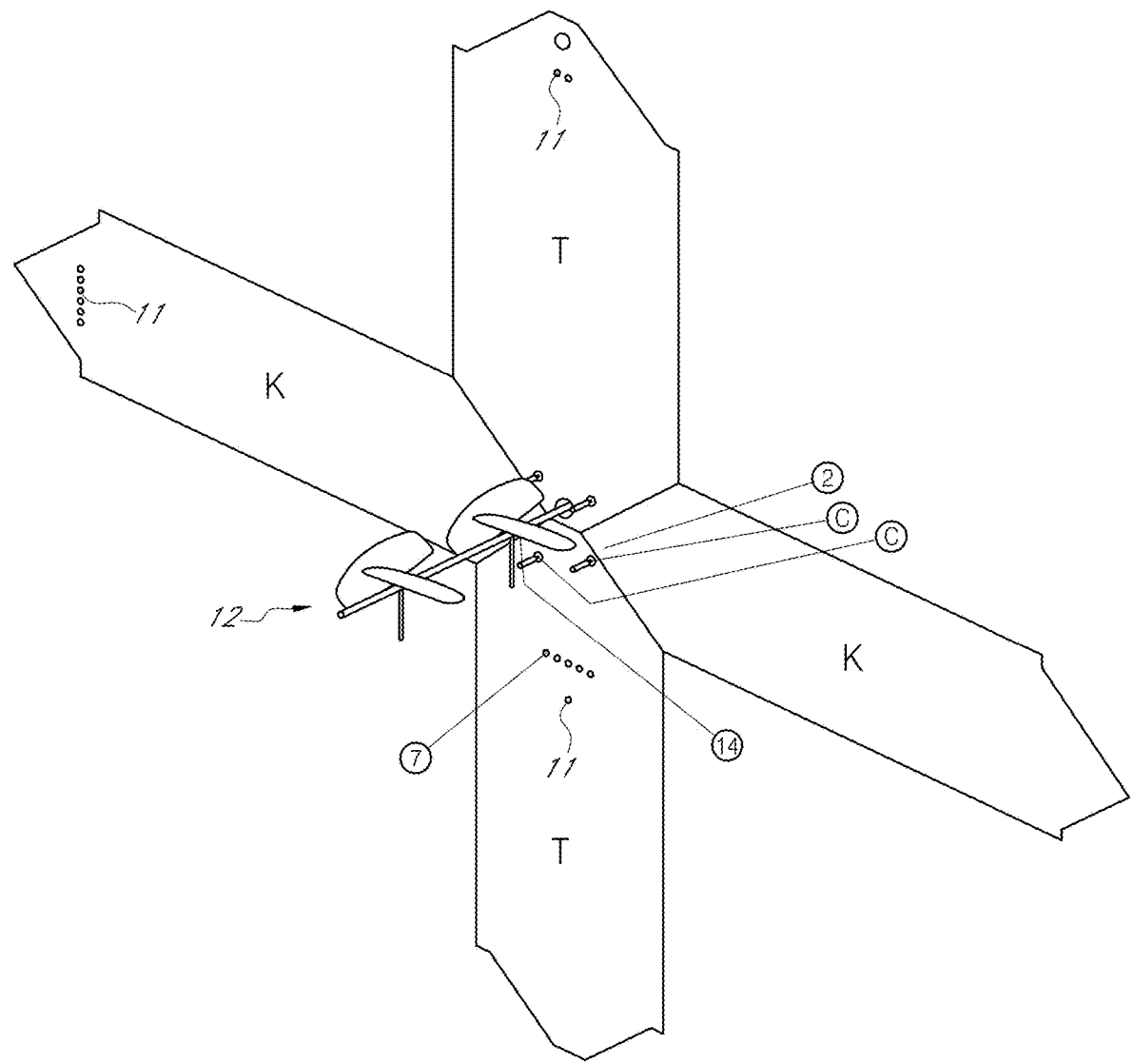
FIG. 14A3

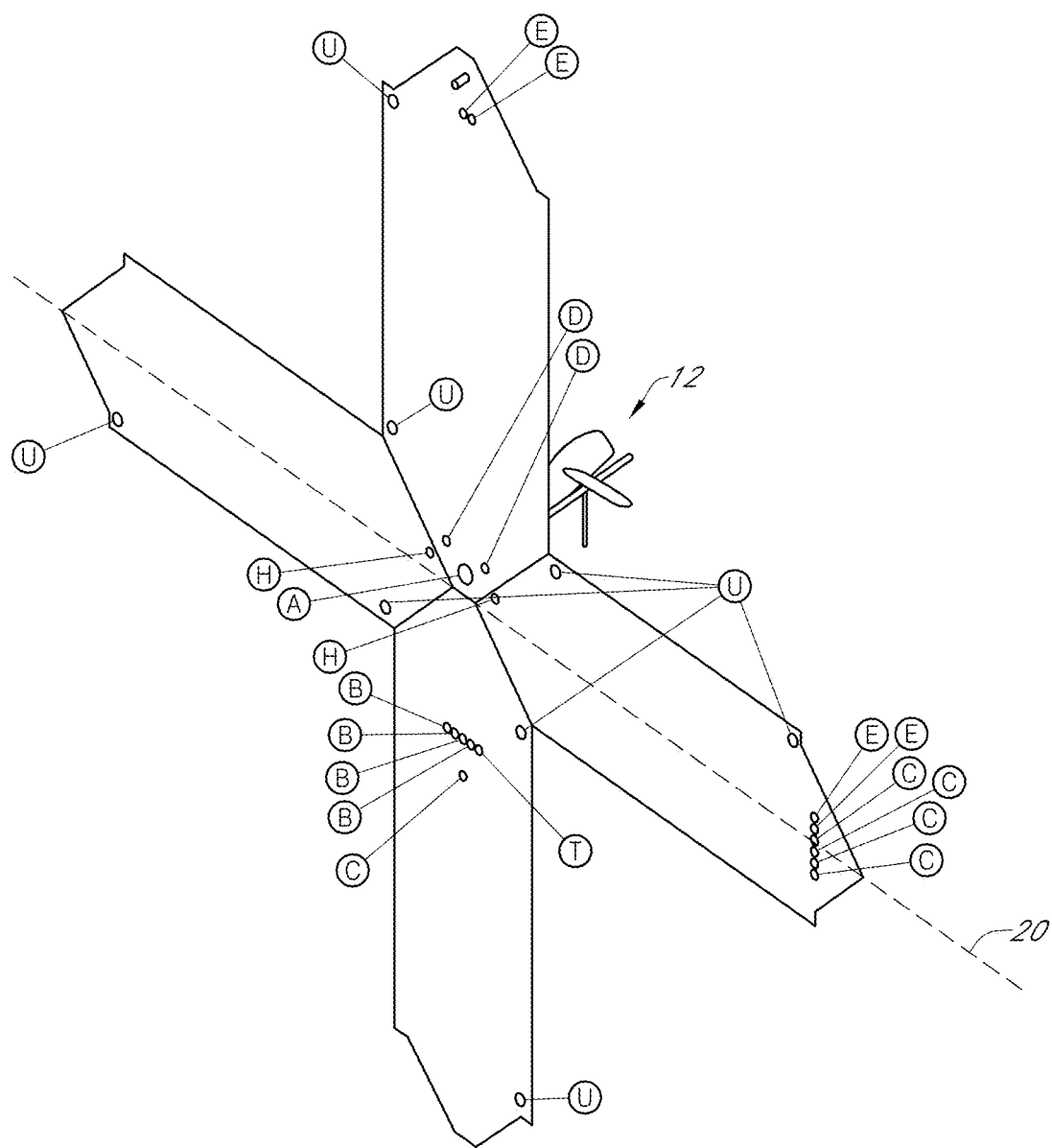
FIG. 14A4

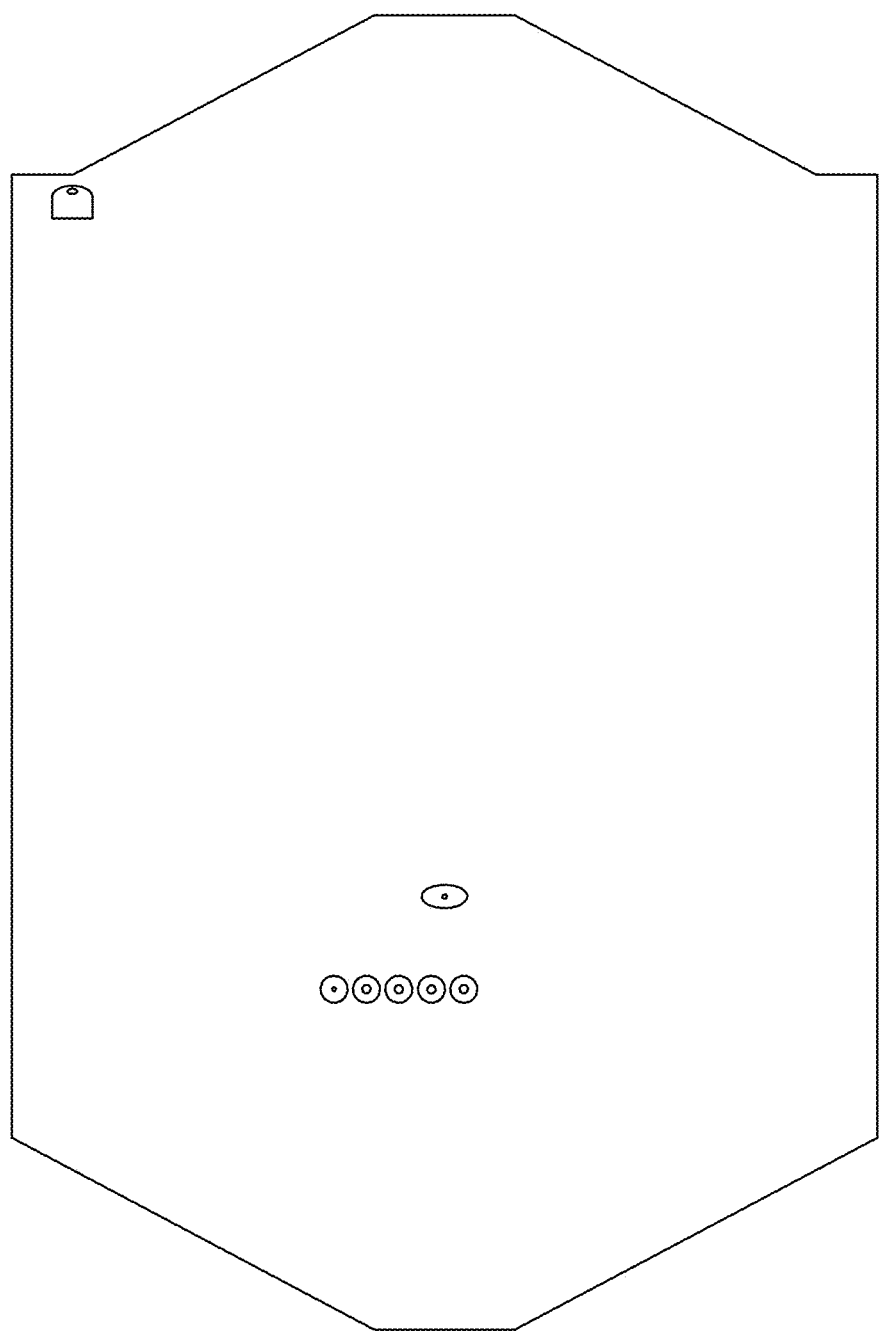
FIG. 14B1

FIG. 14B2

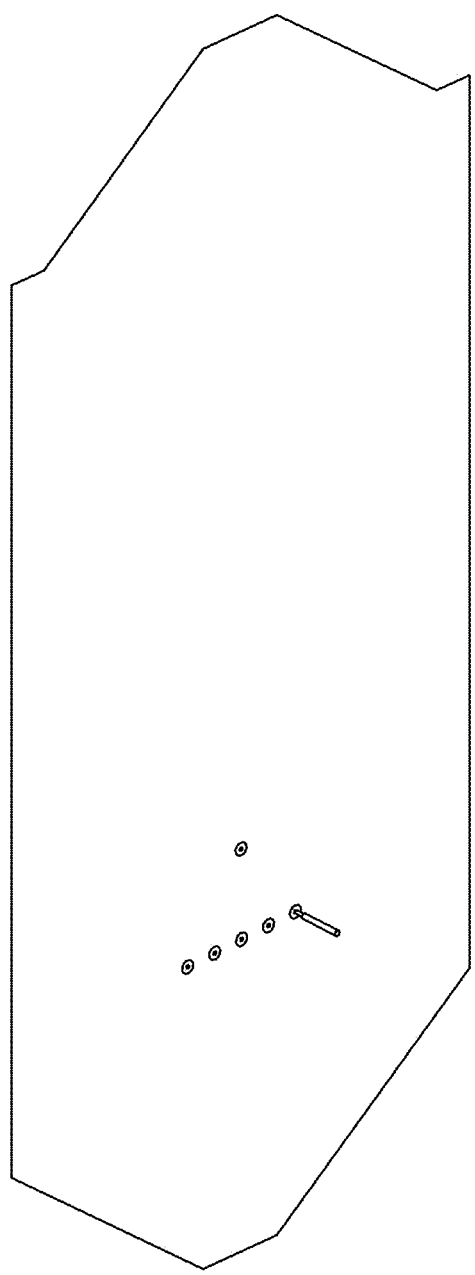
FIG. 14B3

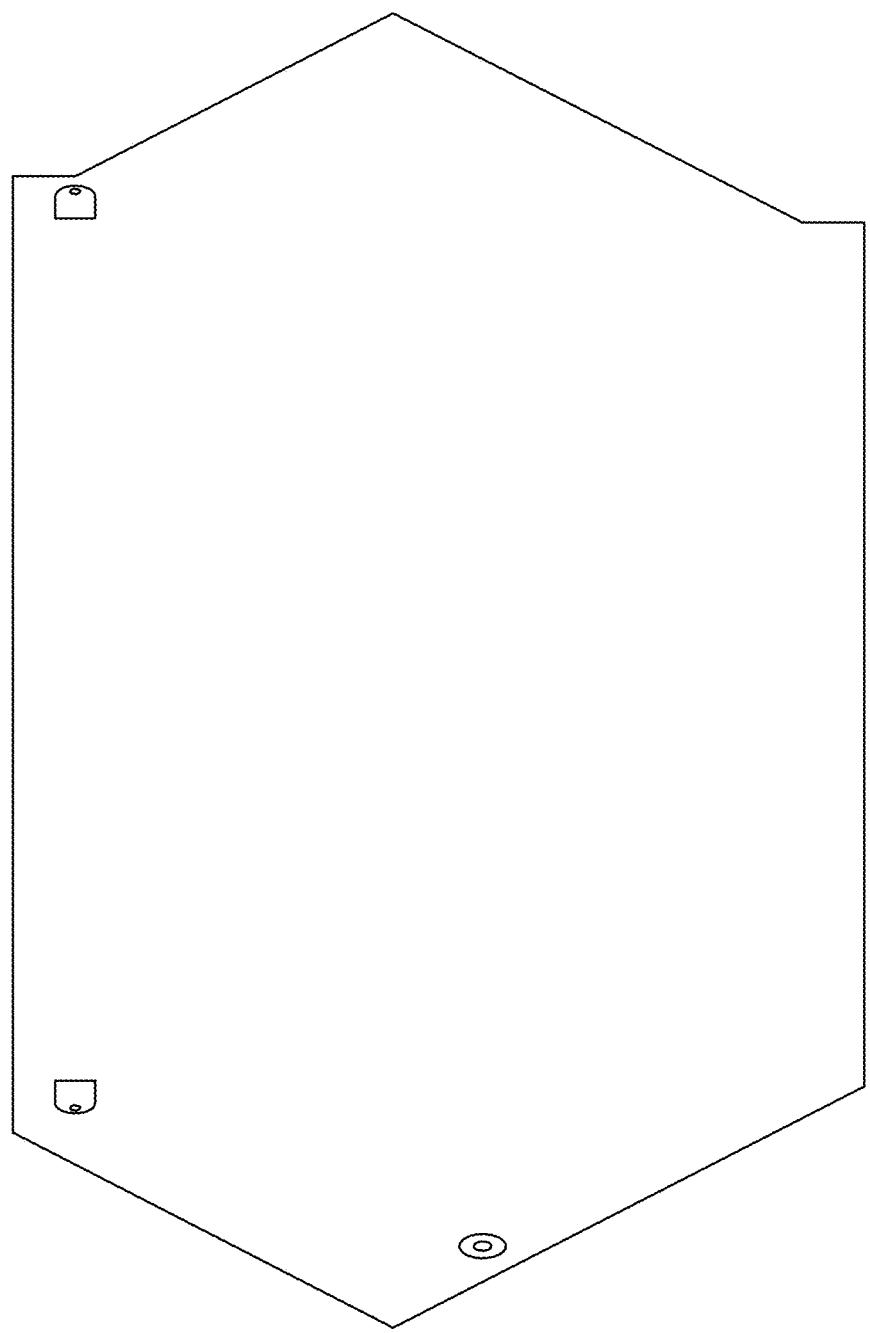
FIG. 14B4

FIG. 14B5

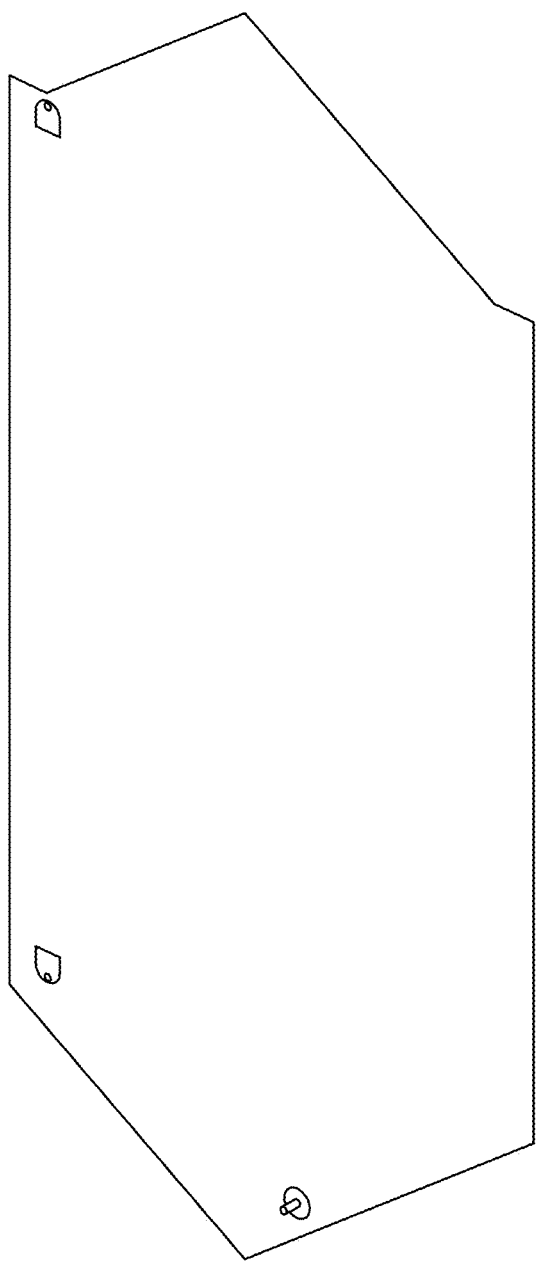
FIG. 14B6

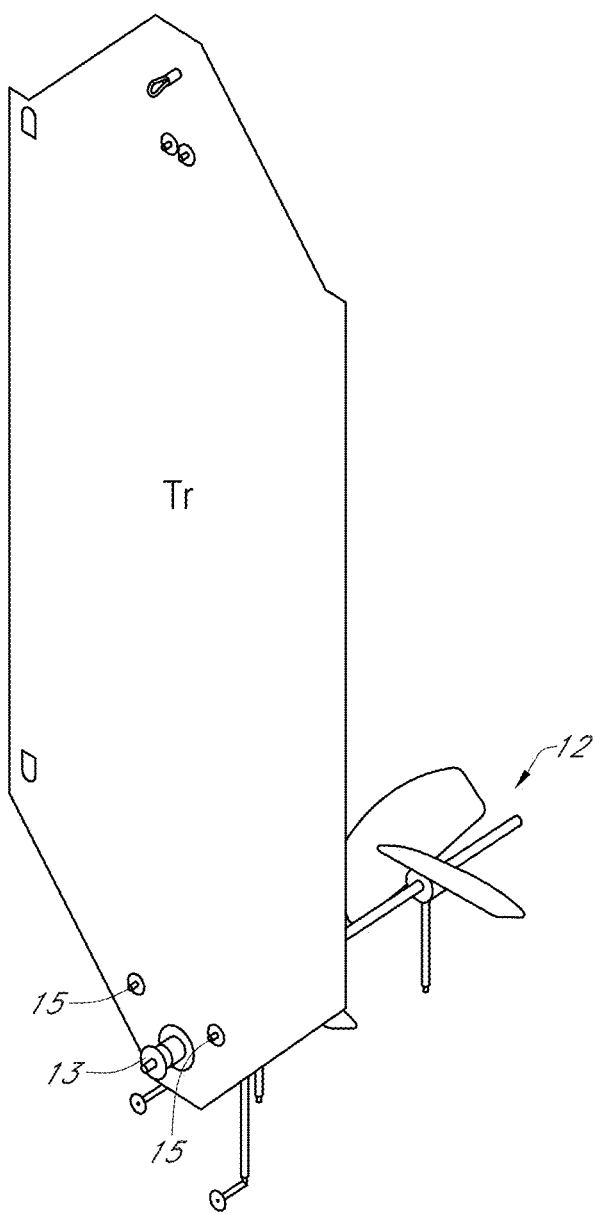
FIG. 14C1

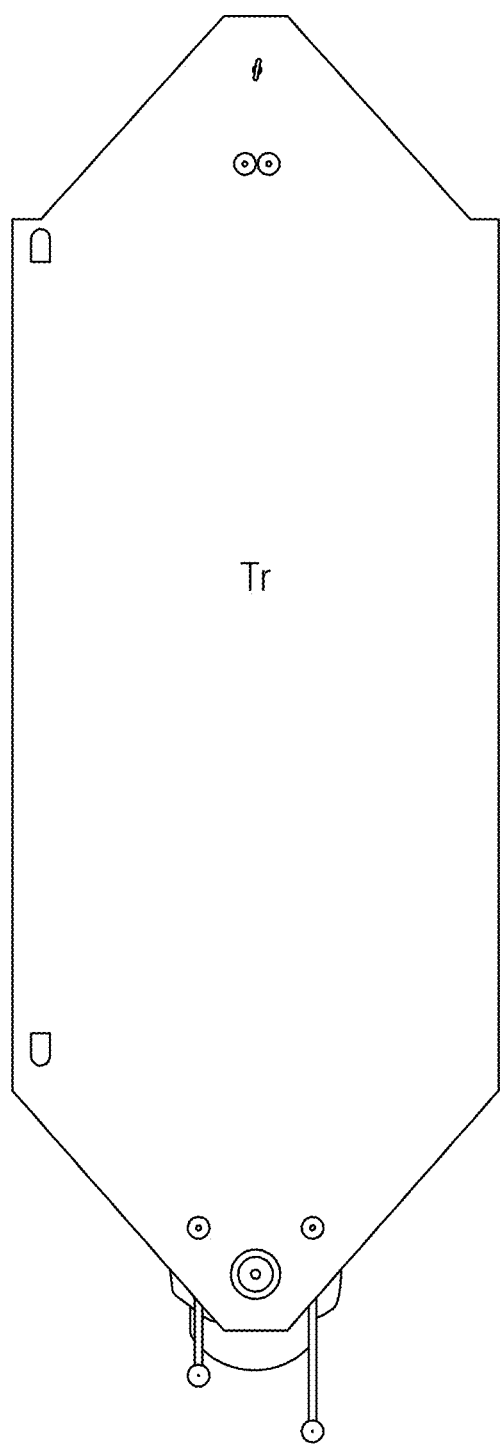
FIG. 14C2

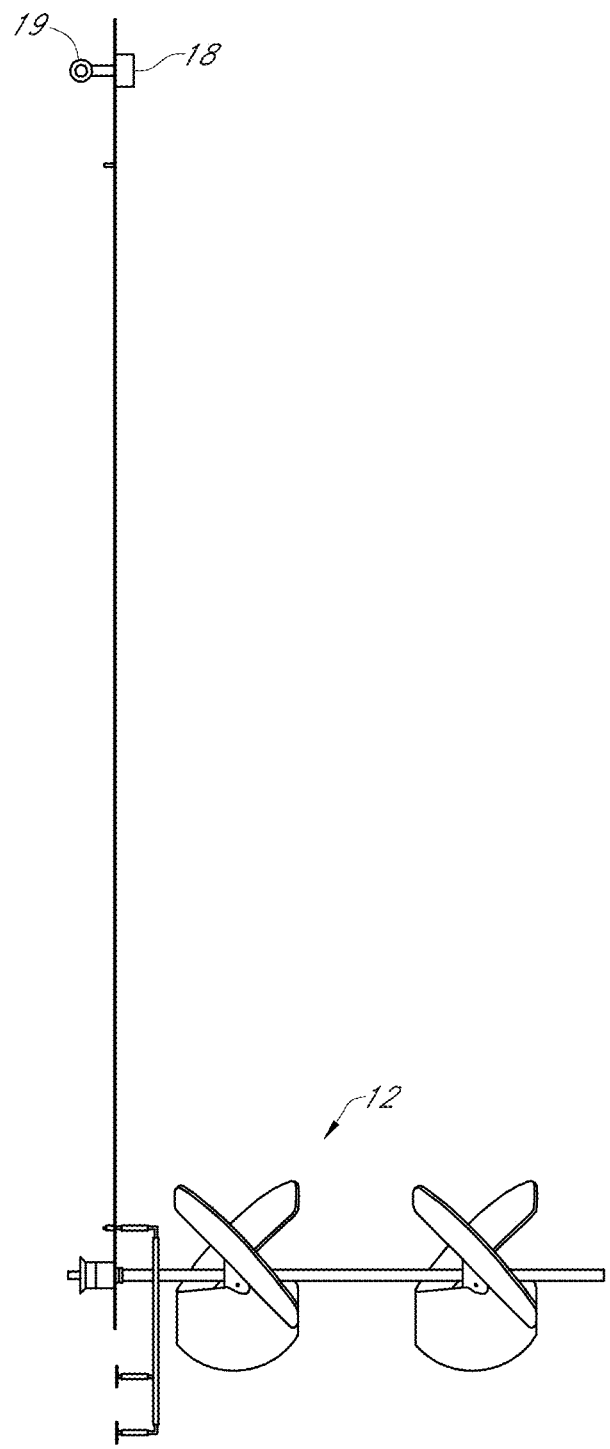
FIG. 14C3

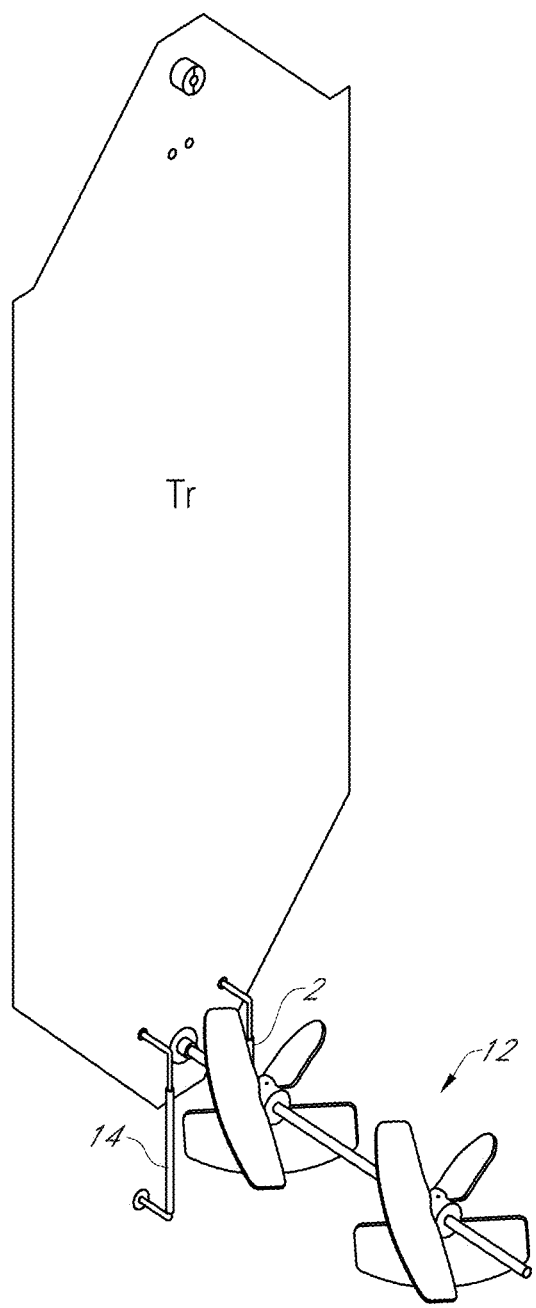
FIG. 14C4

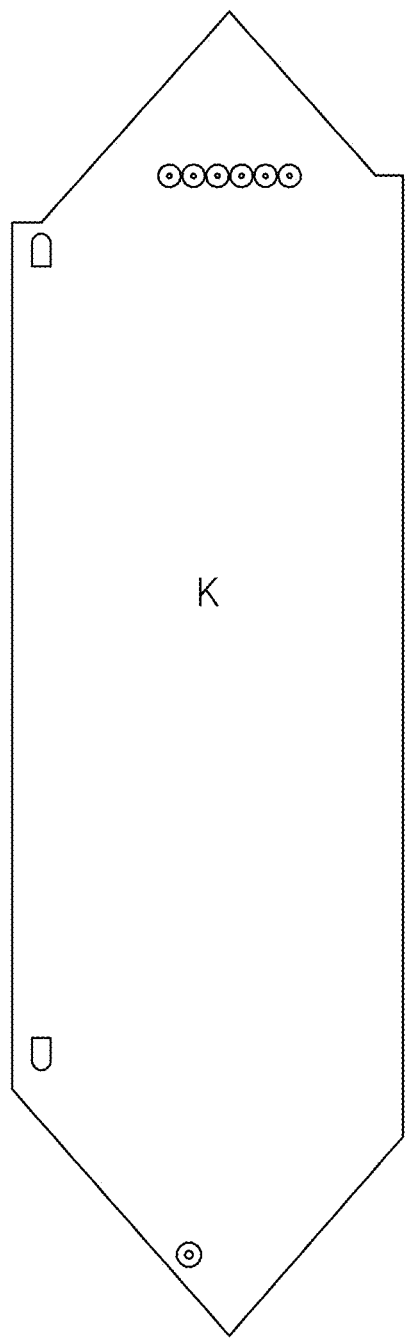
FIG. 14C5

FIG. 14C6

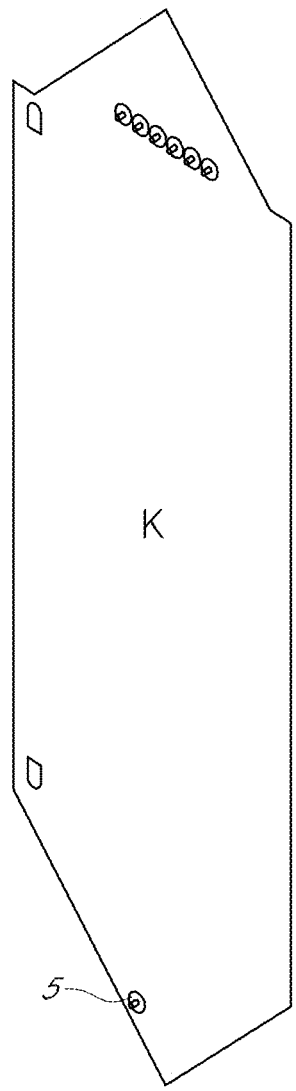
FIG. 14C7

ATTACHMENT DEVICE FOR SINGLE USE CONTAINERS

RELATED APPLICATIONS

This application is a 35 U.S.C. § 371 national stage application of International Application No. PCT/US2014/069320, filed Dec. 9, 2014, and claims priority to U.S. Ser. No. 61/913,960 filed Dec. 10, 2013 and U.S. Ser. No. 62/054,557 filed Sep. 24, 2014, both of which are hereby incorporated in their entirety into this application.

FIELD OF THE DISCLOSURE

This disclosure relates to equipment utilized to manufacture chemical agents, particularly biopharmaceuticals, using Disposable Containers (DCs).

BACKGROUND OF THE DISCLOSURE

This disclosure relates to devices and methods for the manufacture of chemical and/or biological products Such as biopharmaceuticals using Disposable Containers (DCs). For instance, fermentors or bioreactors commonly provide a reaction vessel for cultivation of microbial organisms or mammalian, insect, or plant cells to produce Such products. This disclosure provides improved systems and parts for use in Such systems (or other systems).

BRIEF DESCRIPTION OF THE DRAWINGS

FIG. 14A1. View of DC wall section.
FIG. 14A2. Additional view of DC wall section.
FIG. 14A3. Additional view of DC wall section.
FIG. 14A4. Additional view of DC wall section.
FIG. 14B1. Additional view of DC wall section.
FIG. 14B2. Additional view of DC wall section.
FIG. 14B3. Additional view of DC wall section.
FIG. 14B4. Additional view of DC wall section.
FIG. 14B5. Additional view of DC wall section.
FIG. 14B6. Additional view of DC wall section.
FIG. 14C1. Additional view of DC wall section.
FIG. 14C2. Additional view of DC wall section.
FIG. 14C3. Additional view of DC wall section.
FIG. 14BC4. Additional view of DC wall section.
FIG. 14C5. Additional view of DC wall section.
FIG. 14C6. Additional view of DC wall section.
FIG. 14C7. Additional view of DC wall section.
FIG. 5. Packaging and integrity testing system in use. A. DC/impeller assembly prepared for packaging into PVC container. B. DC/impeller assembly compacted into PVC container. C. Inlet and outlet tubing (e.g., 3 in FIG. 1) of DC attached to top plate. D. Sealed container enclosing DC/impeller assembly attached to water-based integrity testing system.
FIG. 6. Vertical deployment of DC.
FIG. 7. Horizontal deployment of DC. A. Schematic illustrating horizontal deployment of DC. B. DC arranged prior to horizontal deployment. C. DC in the process of horizontal deployment.
FIG. 14. Exemplary DC including assymetrically-positioned implement port.
FIG. 15. Exemplary DC packaging and integrity system (testing).

SUMMARY OF THE DISCLOSURE

Figure 1:
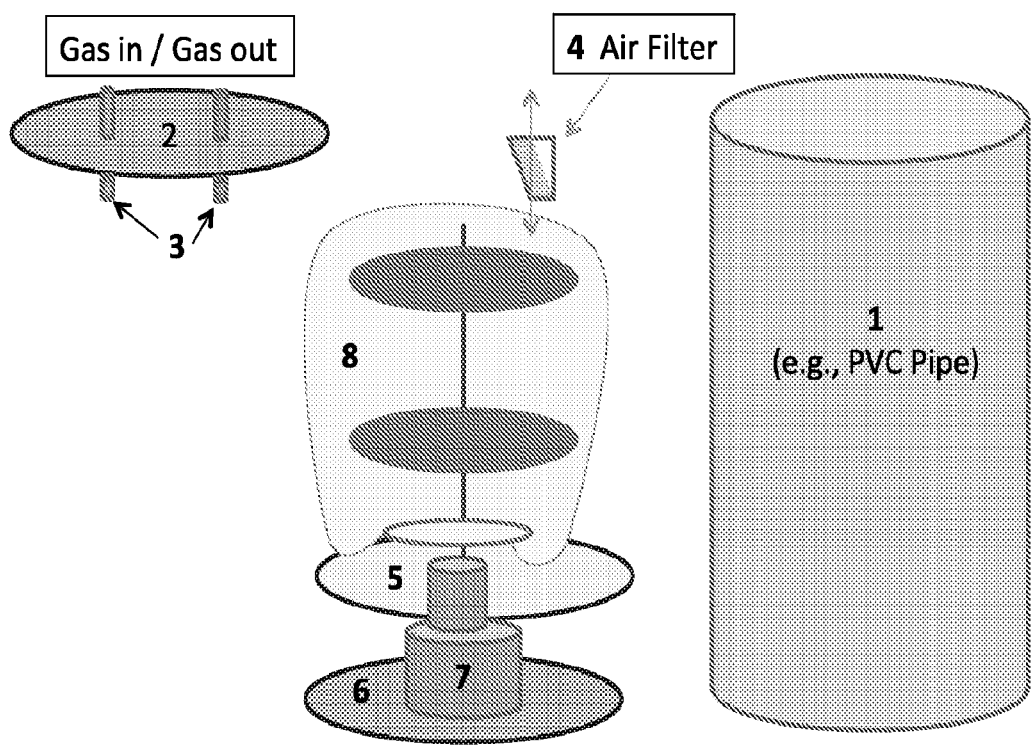
FIG. 1. Exemplary DC packaging and integrity system.

This disclosure provides systems and parts for use in Such systems (or other systems) relating to the manufacture of chemical and/or biological products Such as biopharmaceuticals using Disposable Containers (DCs).

DETAILED DESCRIPTION

This disclosure provides systems and parts for use in Such systems (or other systems) relating to the manufacture of chemical and/or biological products Such as biopharmaceuticals using Disposable Containers (DCs). For instance, in certain embodiments, packaging and integrity systems are described. Vertical and horizontal DC deployment systems are also described. Foam management devices for with DCs are also disclosed. Novel sample ports and seal arrangement are described as well. And improved impellers are described as well. These various embodiments may be combined into a single system or used individually (or in combination) in other systems. Details of these various embodiments are described below.

Packaging and Integrity Testing System

The use of single use containers or disposable container (DCs) in manufacturing processes has increased rapidly in recent years. Maintaining the sterility of DCs during shipment and confirming that sterility has been maintained after delivery remains a challenge. Even very small holes or leaks in the walls and/or seals of DCs may allow contaminants (e.g., bacteria) to enter the container from the environment. Joints and seals between tubing and valves of DCs present a particularly difficult challenge as the chances of a breach in the integrity in such areas is very high. Present tests under pressure are typically conducted with DCs at their inflated volume (e.g., substantially maximal volume).

A common method for leak detection is the pressure decay method. In this method, the DC is first filled with gas to a predetermined pressure. It is then left to stabilize for as much as five to ten minutes, and the pressure is then re-measured. If the pressure has decreased, this indicates that some of the gas has escaped from the container, and the precise drop in pressure can be correlated to the size of the defect (e.g., one or more holes). However, the larger the size of the DC, the less accurate the test becomes as it is difficult to maintain the shape of the DC. An improved version of this test involves constraining the DC in which the DC is pressurized between two plates. The test is rendered more accurate, as an unconstrained bag is more likely to sag and deform, which gives a false impression of the pressure inside. Such methods are typically only useful for detection of defects of a minimum size of about 100 um, which is not sufficient to confirm the integrity of the DC since bacteria can penetrate defects as small as 15 um. Thus, the defect detection limit for DCs must be extended to at least 10 um to ensure contaminants Such as bacteria cannot enter the DC. A similar concept, helium integrity testing, may allow detection of defects down to 10 um. In this method, a DC is placed inside a sealed rigid container and a vacuum is applied. Helium is then injected into the DC and, as has been reported, will escape through defects as small as 10 um. Detection of helium in the container (using, e.g., a spectrometer) indicates the DC has a defect. However, none of these systems provide a comprehensive system for packaging, shipping and integrity testing of DC from delivery to and from initial assembly and upon receipt at client sites.

This disclosure provides a system for testing the integrity of a DC in the original packaging upon receipt by the recipient prior to installation and/or use. As described herein, the system allows the user to test the integrity of the DC at less than full volume (e.g., as DCs are typically shipped) to provide a high level of assurance as to the integrity of the DC. As described herein, the system provides the user the ability to test the integrity of a DC at reduced volume and constant pressure test for integrity where the DC is contained in a vessel. Thus, the test may be applied to detect leaks in DCs at inflation pressures at deflated chamber volumes. As described herein, the DC flexible components are typically configured/arranged by folding/rolling (with or without spacing materials) wherein the physical volume is reduced and the surface area of the DC is maintained to allow for gas flow through defects to pass and be collected in the vessel and measured. In this system, the packaging material serves as a reservoir to collect any gas which leaks from the DC and channels this to a flow measuring device whereby the defects can be quantified to off-set initial equilibration of the package and DC, and as the DC is inflated and the air/gas from the packaging is displaced.

In some embodiments, this system includes a device for simultaneously providing for packaging and integrity testing of DCs (e.g., disposable bioreactors) is provided. These devices provide a non-destructive way to test DC's such as disposable bioreactors and related systems after manufacture and packaging, and prior to installation. Certain embodiments provide a first container enclosing a DC where the first container comprises a top surface, a bottom surface, and a sterilizable (or sterile) interior volume. The first container also preferably includes an outlet, and an inlet comprising a filter. The bottom surface of the first container also preferably comprises a pedestal upon which the inflatable container may be supported. The DC is typically sterilizable (or sterile) and may be positioned upon or supported by the pedestal. The first container is arranged to constrict the volume of the DC. The filter may maintain the sterility within, and/or allow air/gas to enter the interior volume. The integrity of the DC may be tested by filling the same with air/gas through the inlet and measuring the release of air/gas from the DC through the outlet. "Integrity" refers to the maintenance of an air/gas tight condition of the DC. The integrity of the DC may be confirmed by the failure to detect any release of gas and/or liquid from the DC into the first container which surrounds the first container. Integrity may be tested at partial and/or full volume capacity (e.g., of the DC). The first container provides support to the DC Such that it may be inflated at less than its full volume and test the entire surface of the second container for defects (e.g., mechanical defects). Integrity may also be tested at elevated pressures, e.g., above those pressures the second container typically encounters when used in practice (e.g., a fermentation reaction). Release of the gas and/or liquid may be detected by any method known to those of ordinary skill in the art.

Figure 2:
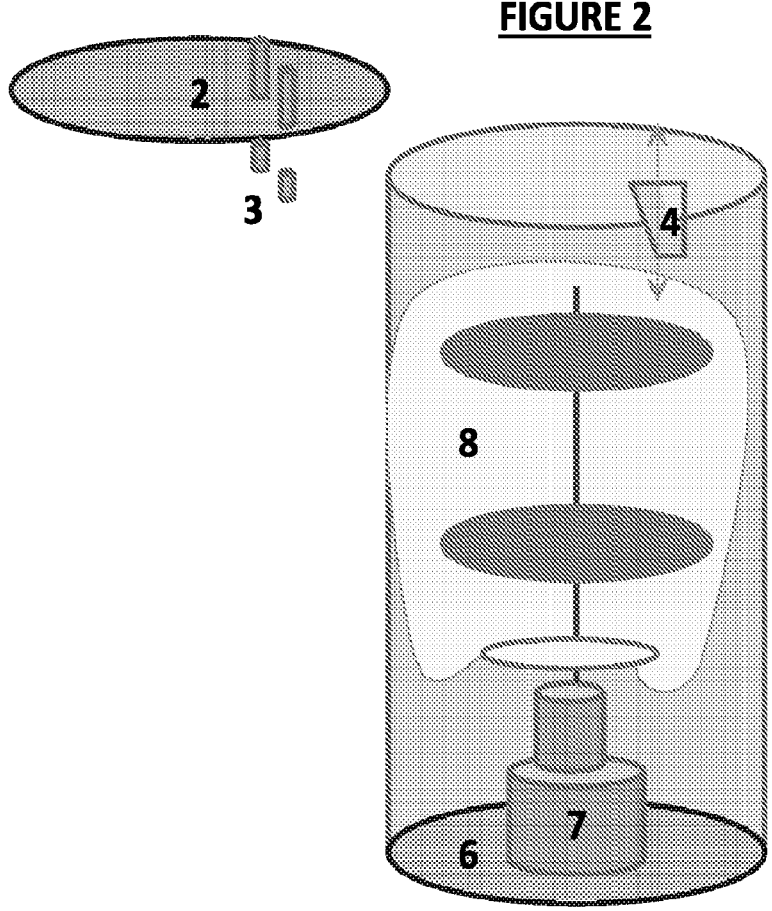
FIG. 2. Exemplary DC packaging and integrity system (assembly in process).
Figure 3:
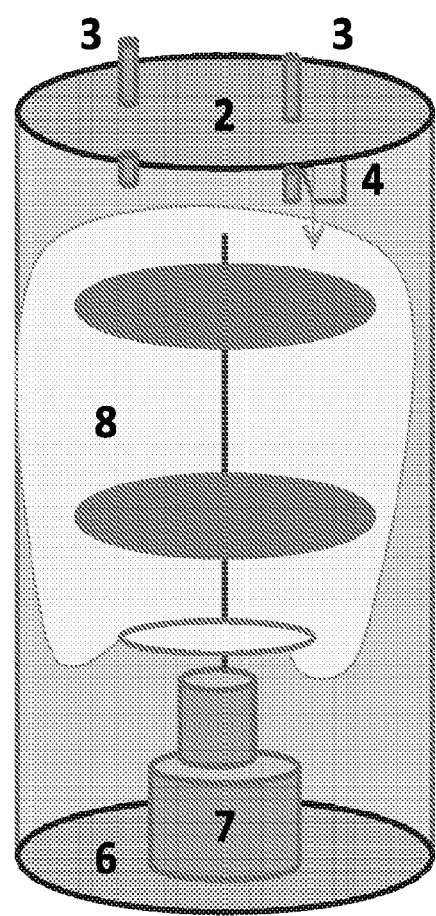
FIG. 3. Exemplary DC packaging and integrity system (assembled).
Figure 4:
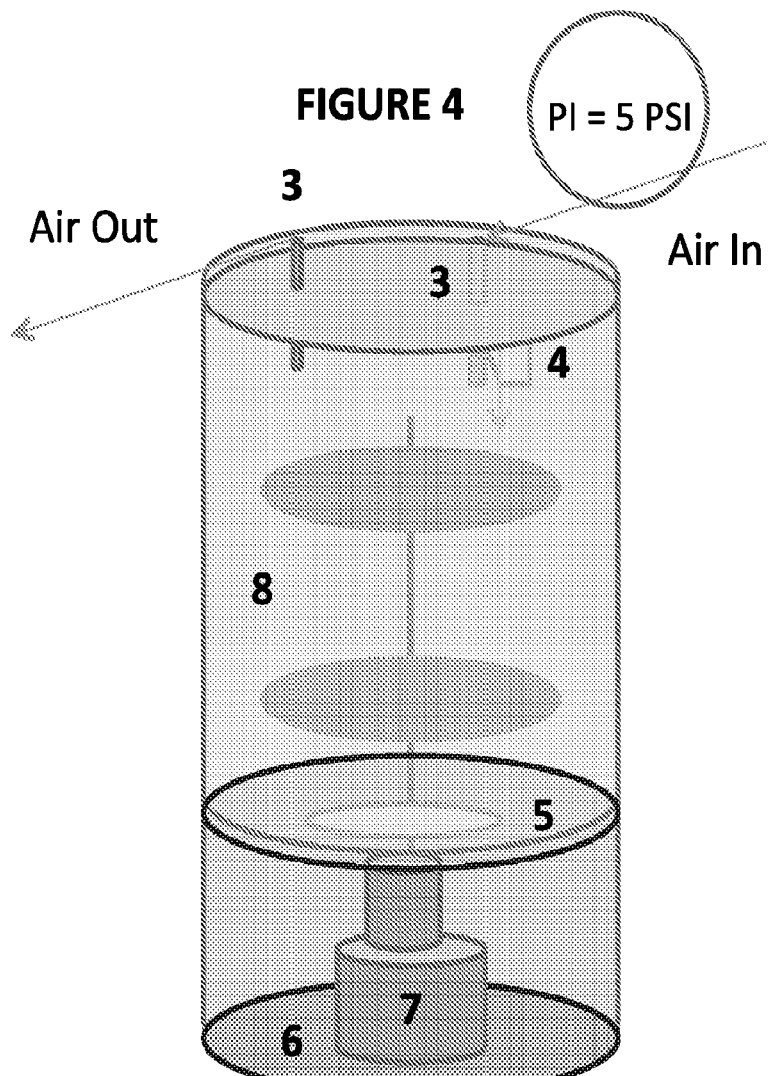
FIG. 4. Exemplary DC packaging and integrity system (testing).
Figure 5:
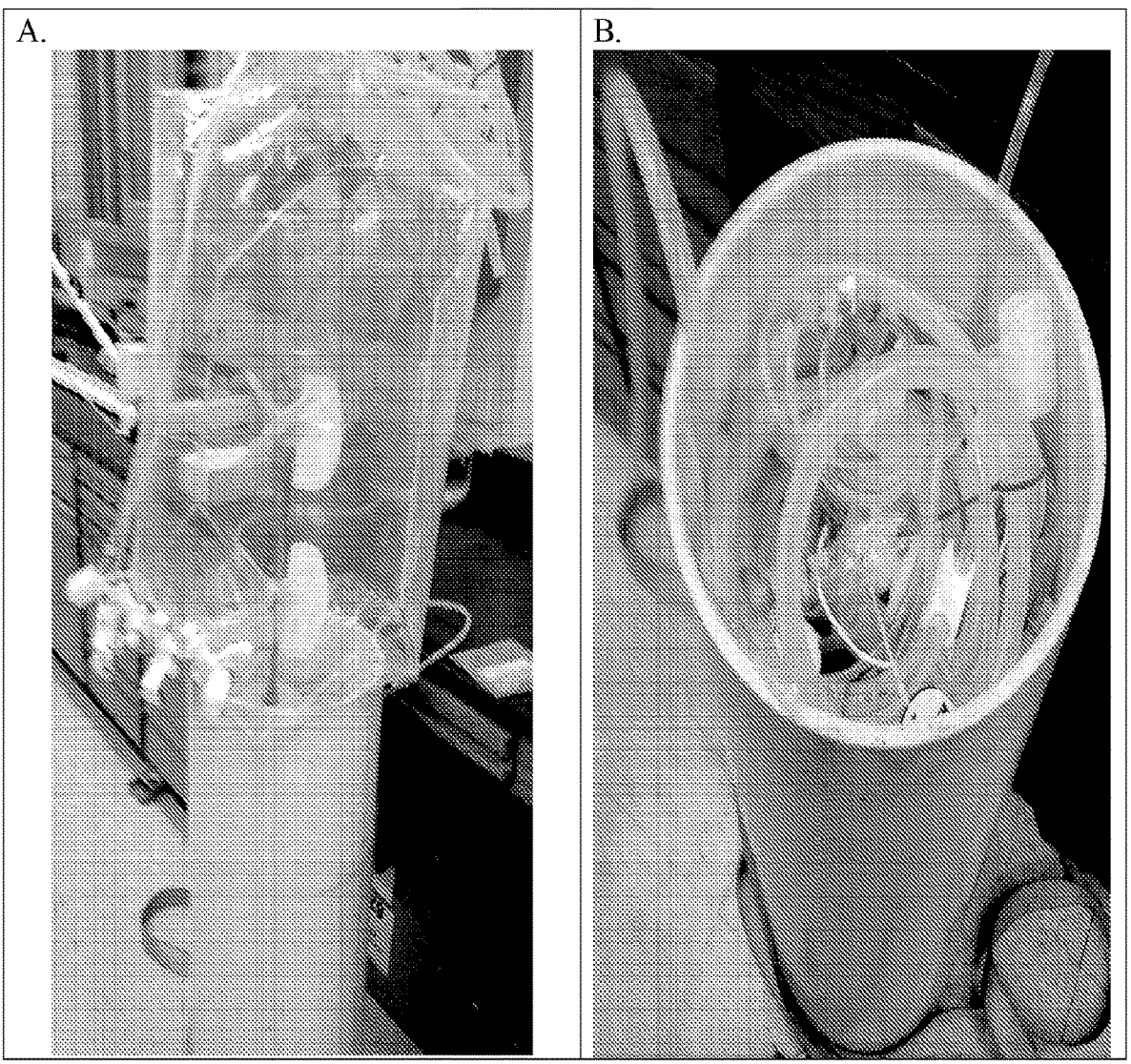
Figure 5:
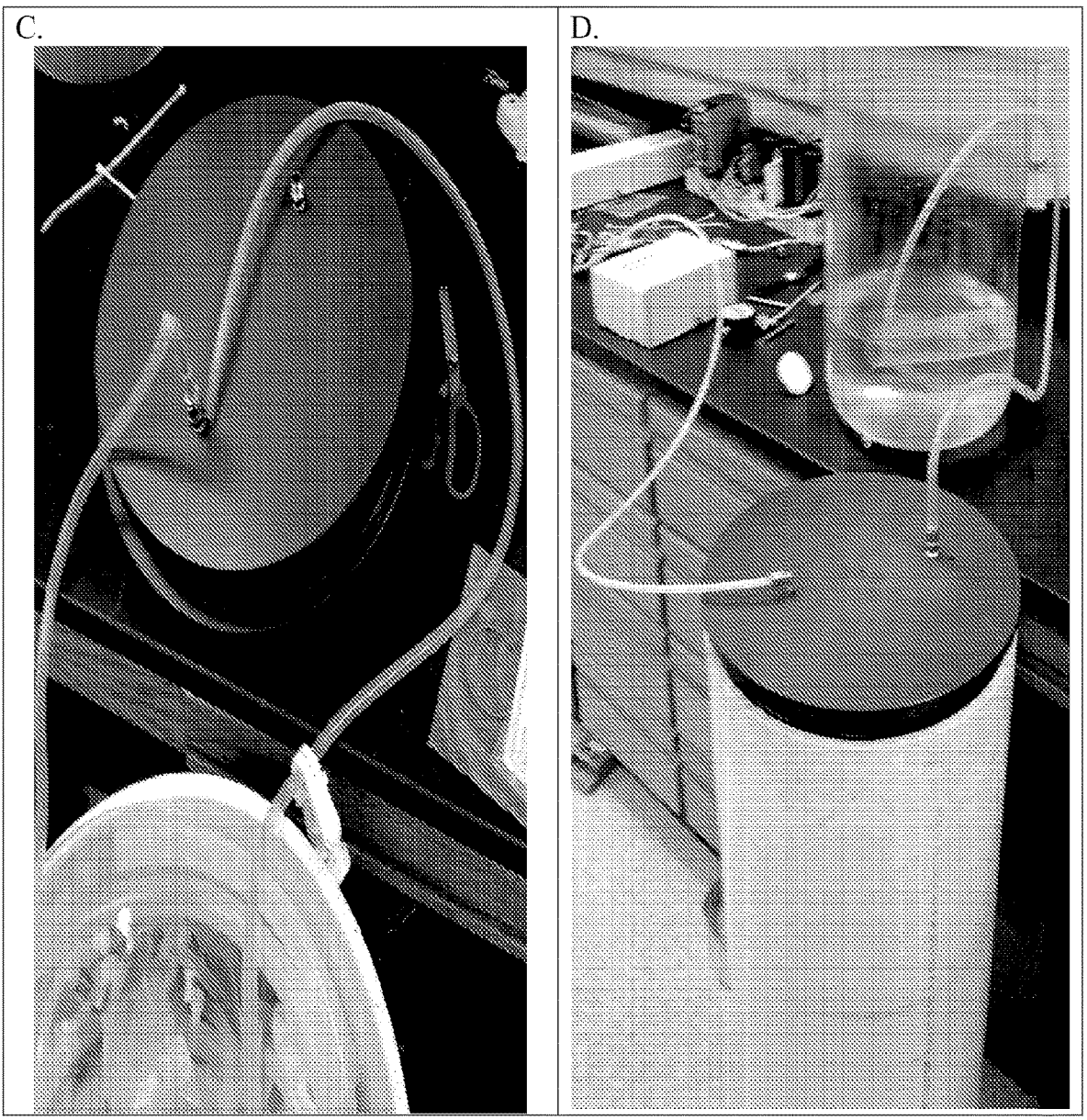

FIGS. 1-5 illustrate a particular embodiment of a packaging and integrity testing device. As shown in FIG. 1, the device may comprise a container 1 (e.g., pipe such as a PVC pipe of sufficient diameter to enclose a DC), top plate 2 (e.g., removable) comprising a flange with at least one pipe 3 protruding through the top and bottom of the surface thereof (e.g., in communication with the exterior and interior of container 1) (see also FIGS. 5C-D), gas filter 4 affixed (e.g., removably affixed) to the interior portion (e.g., relative to the container) of at least one of said tubes 3, support plate 5, and bottom plate 6 comprising a flange (see also FIG. 5A). Bottom plate 6 may also comprise or be in contact with a mount 7 (e.g., a pedestal) for a mixer assembly. The mount may also be in contact with support plate 5, and/or be positioned between support plate 5 and bottom plate 6. DC 8 is typically mounted upon support plate 5 (e.g., optionally along with the mixer assembly such as an impeller and support components). FIG. 2 illustrates a partially assembled device; top plate 2 comprising two pipes 3 is shown ready for attachment to container 1 in which DC 8 is mounted upon support plate 5 which is mounted upon mount 7 which is attached to bottom plate 6 (see also FIG. 5B). FIG. 3 illustrates the device in the closed configuration (e.g., ready for shipment and/or integrity testing). FIG. 4 illustrates the gas flow pattern into and out of the container during integrity testing (see also FIGS. 5C-D). As illustrated therein, gas may be introduced into container 1 through air filter 4 via, for instance, the exterior portion of tubing 3 (e.g., the nipple thereof) and the container pressurized to an appropriate psi (e.g., 1-5 psi). The pressure is typically held for an appropriate amount of time (e.g., any of 1-100 minutes) and any pressure drop over that time noted. Any pressure drop (e.g., gas flow out) may be measured using an inverted cylinder in water or other liquid. In some embodiments, the container may be pressurized, the DC filled with gas, and any gas that escapes may collected in the container and directed to a detection device (Gas Rotameter, Inverted Graduate Cylinder) in a manner consistent with integrity testing of membrane filters. If no significant pressure drop (e.g., when using a water-based detection system, if one or more bubbles are observed) is detected, one may conclude that the DC does not have any leaks (e.g., it is integral). This is a significantly more sensitive than current integrity tests and may be performed during installation.

Packaging and Integrity Testing System (Vacuum Test)

Figure 6:
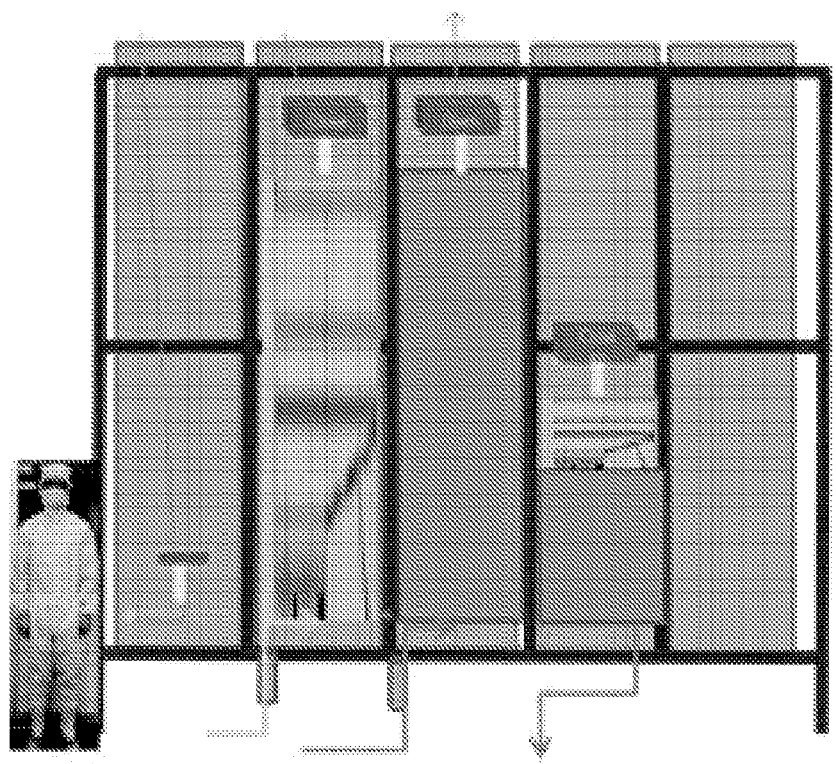

An alternative test methods to applying positive gas pressure into the DC, negative pressure or Vacuum can be used along with to create a potential leak into the DC which can be detected by means internal to the DC such as with a residual amount of suitable liquid which when directed over seams within the bag can serve to obviate bubbles which would be due to a non-integral seal of defect in the DC. An alternative means to detect would be with gas or vapor challenge (e.g. Propylene Glycol) source external to a DC with a means of detection either instrument (e.g. helium detector) or visual within the DC Vertical Deployment System DCs positioned vertically within a container are typically filled from the bottom to the top using a mechanical device that serves to raise the DC as it is being filled. In this way, the DC may achieve its full volume without being impeded by wrinkles and the like in the DC material as it is being filled. Typically the DC is vertically raised in the container using a hoist or other type of equipment for providing a lifting/stretching force on the DC as it is being filled. Although these types of systems are widely used in the industry, the use of equipment to raise the DC as it is being filled presents various problems such as the risk of tearing the DC film. To solve such problems, this disclosure provides a vertical DC deployment system that operates without the application of any vertical (e.g., upward) force on the DC. Instead, this disclosure provides a vertical deployment system comprising an apparatus including a housing comprising an internal volume and an at least partially open bottom panel for positioning a DC prior to filling and supporting the DC during and after filling; and inlet and outlet tubing (e.g., each typically comprising a sterile filter and valve(s) attached to the DC through the at least partially open bottom panel, the inlet and outlet tubing each comprising a sterilizing filter and valve(s)). The DC may be filled with fluid (e.g., already sterile or that is sterilized as it moves through the inlet tubing sterile filter) through the inlet tubing; and, as the DC is filled, the volume thereof expands into the internal volume of the housing vertically without application of additional upward force on the sterile DC. An embodiment of the vertical deployment system is illustrated in FIG. 6.

Horizontal Deployment System

As described above, DCs positioned vertically within a container are typically filled from the bottom to the top using a hoisting mechanism that serves to raise the DC as it is being filled. In this way, the DC may achieve its full volume without being impeded by wrinkles and the like in the DC material as it is being filled. However, in some settings it would be beneficial to fill the DC horizontally. This may be accomplished by, for instance, positioning the DC at one end of a horizontal container and filling the DC such that it expands horizontally across the container. The DC may be in any configuration prior to filling but one particularly useful configuration may be as a roll. If filled from the rolled configuration, the DC may conveniently unroll horizontally across the horizontal container. In some embodiments, the horizontal container may be a horizontal holding tank comprising a housing comprising an at least partially open panel and a closed panel; a rolled sterile DC positioned adjacent to the at least partially open panel of housing; and, inlet and outlet tubing protruding through the at least partially open end of the housing. Typically, the inlet tubing comprises a sterile filter such that any fluid entering the DC would be (e.g., or become) sterile. This device may therefore be used by positioning a rolled sterile single use container proximal to the partially open panel and distal from the closed panel. The DC is then filled with a sterile fluid (e.g., either already sterile or sterilized as it passes through the sterile filter) through the inlet tubing such that it unrolls horizontally from the partially open panel toward the closed panel of the housing as it is filled. Embodiments of this horizontal deployment system are illustrated in FIG. 7A-C.

Foam Management Device

Another challenge when using DCs is filter fouling due to foaming during the reaction, which can interfere with the venting of gasses from the DC. In some embodiments, this disclosure provides an anti-foaming device comprising a chamber comprising an internal volume having a tortuous path formed by static mixer and/or granules within, where the static mixer and/or granules are composed of a sterilizable material. The chamber is attachable to a DC at one end and a vent at another end to form a passage between the DC and a sterile vent filter arrangement comprising one or more filters. The DC typically holds fluid for a reaction that produces gas that needs to be exhausted without also losing any of the fluid or allowing the fluid or foam derived therefrom to interfere with the release of gas from the DC. Using the device described herein, foam is prevented from reaching the filters thus assuring a passage is provided through which the gas may be vented and in the process to reach the vent. During transport through the chamber, any foam (e.g., fluid comprising one or more bubbles) is removed such that only gas exits the anti-foaming device and is expelled from the chamber (e.g., into the atmosphere). Where fluid in the form of a foam is present in the gas stream, for instance, the foam therein will be destroyed (e.g., any bubbles will be "popped") as it moves through the anti-foaming device such that only gas exits the device and reaches the vent.

Figure 8:
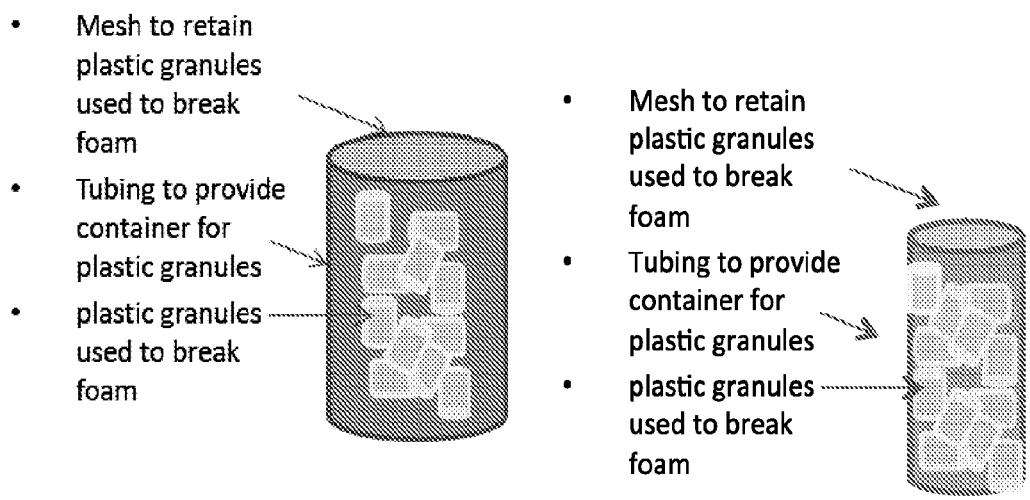
FIG. 8. Exemplary foam management device.

FIG. 8 illustrates an exemplary embodiment of the anti-foaming device. As illustrated therein, in this embodiment, the interior volume of a chamber contains static mixer and/or granules (e.g., tortuous path) that collapse the foam (e.g., in the form of bubbles) that enters the device. The device typically includes an inlet receiving surface and a venting surface positioned opposite one another on either side of the chamber. The tortuous path are found within the chamber between the inlet surface and the venting surface. The chamber may be in the form of tubing (e.g., plastic tubing), for example. Each of the gas inlet surface and the venting surface may be comprised of a material (e.g., a porous and/or mesh material) which serves to retain the granules within the container. The material comprising the surfaces may thus serve to compartmentalize the granules, thereby forming a container. In some embodiments, the anti-foaming device may be contained within a portion of tubing connected to the DC between the exhaust port at the top of the DC and before the exhaust. In such embodiments, the anti-foaming device does not necessarily need to form a completely separate piece of equipment that may be attached to the venting tubing, for instance. Instead, the anti-foaming device may be formed by positioning the material at either ends of a section of tubing that contains tortuous path. One piece of said material may be positioned within the tubing to be proximal to the DC and distal to the vent, and functions as a gas stream receiving surface. Another piece of material may be positioned within the tubing to be proximal to the vent and distal to the DC, and functions as a venting surface. The tortuous path are positioned between the gas stream receiving surface and the venting surface. In some embodiments, the tortuous path, the tubing, the material, and/or the DC are composed of substantially the same material. Alternatively, the device may be manufactured and then inserted into the tubing, for instance. Other embodiments are also contemplated herein, as would be understood by those of ordinary skill in the art.

Seal Arrangement and Housing

Figure 9:
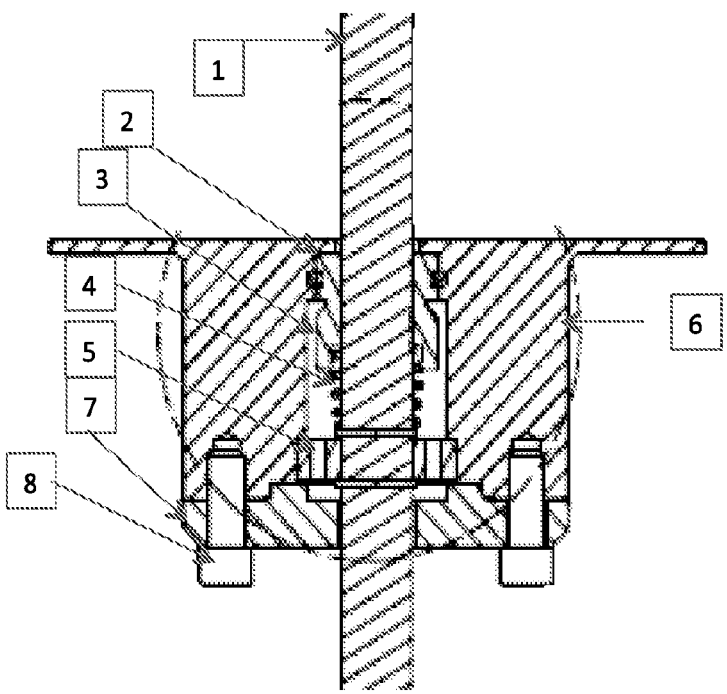
FIG. 9. Exemplary seal arrangement.

In some embodiments, a seal and seal Housing (e.g. Disposable Seal Housing (DSH)) may be incorporated integral to the DC. FIG. 9 illustrates an exemplary DSH comprising static seal face (2), rotating seal face (3), seal spring (4), bearing (5), seal housing (6), seal housing cover (7) and retaining screw (8) affixed (e.g., removably affixed) to a shaft (1) of an impeller. Adaptations to traditional mechanical seals have been made in order to deploy such seals in DCs. For instance, in one embodiment, mechanical seal arrangement is enclosed in a DSH and energized within the housing enclosure. Thus, the seal is maintained within the DSH and associated shaft which may then be attached to other components of the DC to create a closed system suitable for sterilization. This disclosure enables the seal to be energized within the seal housing throughout the fabrication, sterilization, transport and use of the DC.

Low Profile Seal Housing

Figure 15A:
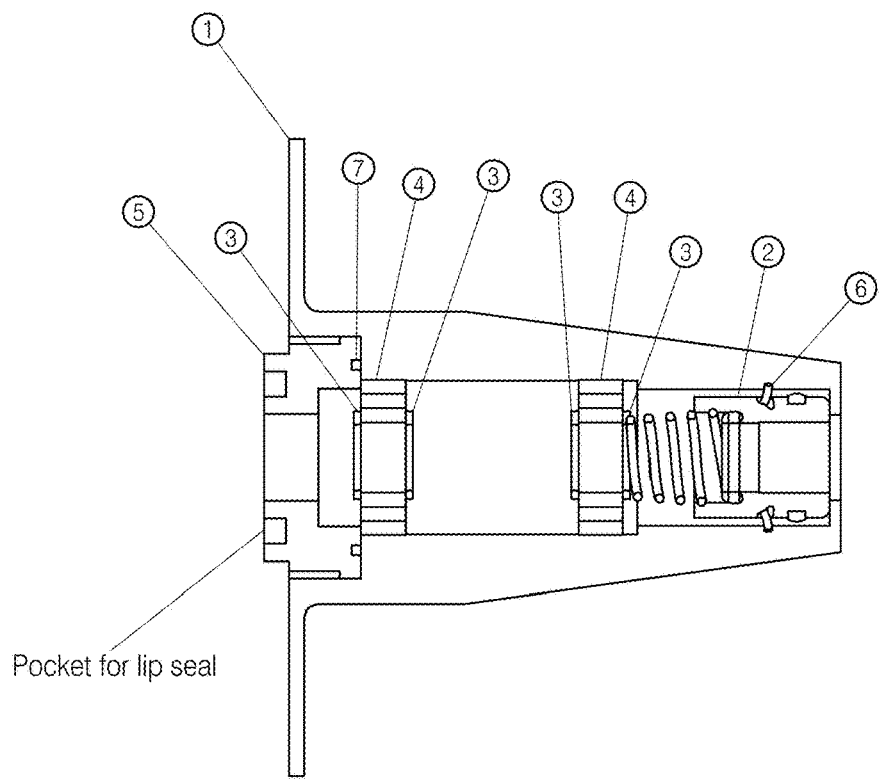
FIG. 15A. View of low profile seal housing.
Figure 15B:
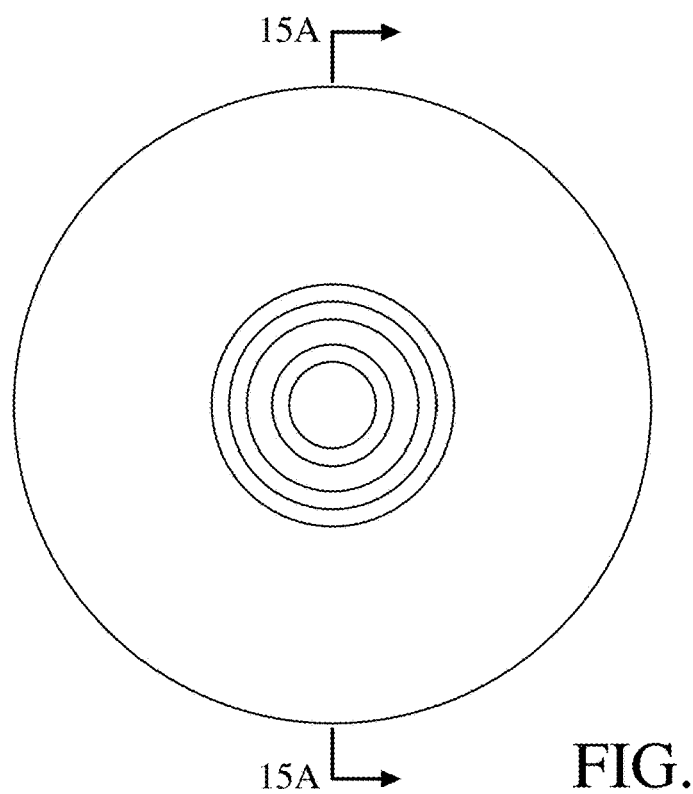
FIG. 15B. Additional view of low profile seal housing n.
Figure 15C:
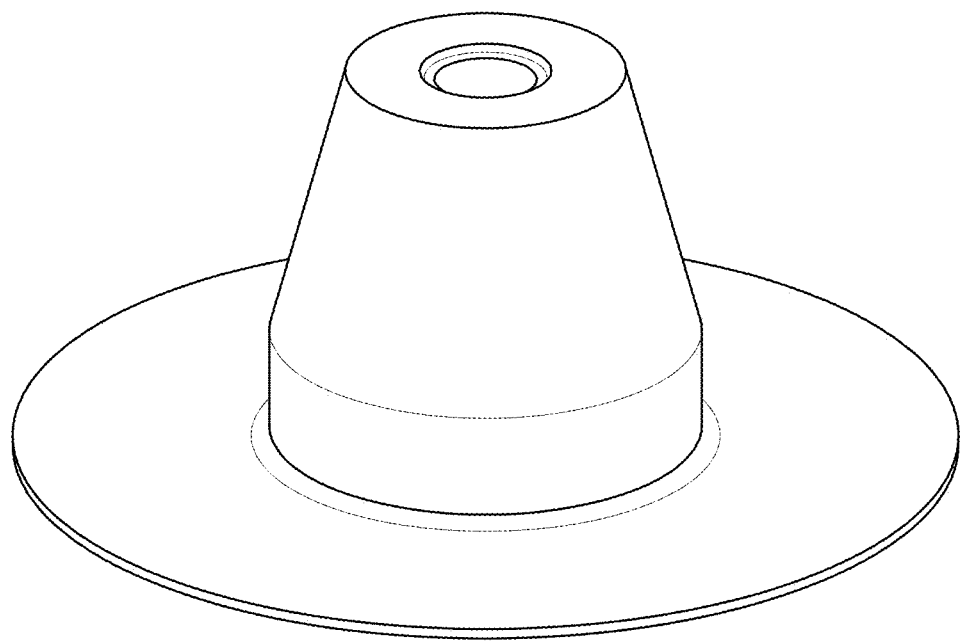
FIG. 15C. Additional view of low profile seal housing.

DCs typically incorporate fixtures for rotating equipment which are mechanically driven and may be sealed using various types of mechanical seals. However, there is limited space upon the DC to locate such seals and other restrictions on positioning such as seam locations. To solve such problems, this disclosure provides embodiments in which housing of the seal is positioned within the space of the DC (e.g., the interior space) thereby minimizing the external profile of the fixture. This provides multiple advantages such as, for instance, simpler handling and more efficient positioning of the fixture. An embodiment of such a low profile seal housing is illustrated in FIG. 15. As shown in FIG. 15A, this exemplary housing includes internal seal housing 1, seal shaft 2, first retaining rings 3, bearing balls 4, internal seal housing retainer 5, second retaining ring 6 and O-ring 7. The exemplary housing further comprises a pocket(s) for using one or more lip seals and/or additional mechanical seals to seal the housing to the DC.

Detachable Coupling Devices

Difficulty is also often encountered in configuring DCs and the various devices required to carry within the DC. For instance, DCs may be used with various types of stirring mechanisms. Exemplary stirring mechanisms may be, for instance, impellers. Typically, a DC constructed around an impeller or impellers integral to the DC. This presents difficulties with respect to fabrication, packaging, shipping, sterilization, and/or general handling of the DC. This disclosure provides solutions to these problems. An exemplary solution is a detachable coupling device comprising an attachment point outside the DC and a detachable point inside the closed DC. This detachable coupling device may also be used to facilitate lifting of an apparatus (e.g., mixing shaft and assembly, perfusion apparatus) to be inserted into a DC. During assembly, the detachable coupling device may be used to handle a large apparatus to avoid damage to the DC film. The detachable coupling device thereby allows, for example, the user to lift and center a large mixing device to be manipulated prior to, during, and after DC fabrication without decoupling the coupling device from the shaft. In some embodiments, this disclosure provides a DC comprising at least one attachment mechanism that may include at least two parts, one positioned within the DC and one positioned exterior to the DC. Upon attachment to one another, the interior and exterior parts may form a single, two-part attachment mechanism. The interior part of the mechanism would typically attached to an impeller and any supporting components thereof. The DC, internal attachment mechanism and other components (e.g., the impeller) may be sterilized together prior to use. In some embodiments, then, the present disclosure provides a DC comprising an internal volume, a container comprising an attachment mechanism comprising a first attachment mechanism at least partially positioned within the internal volume of the DC and a second attachment mechanism positioned on the exterior of the container. The first and second attachment mechanisms may be reversibly attached to one another. The first attachment mechanism may further comprise an attachment mechanism for reversibly attaching a device contained within the internal volume of the DC thereto. The second attachment mechanism may further comprise an attachment mechanism for reversibly attaching a device exterior to the container thereto. Embodiments of detachable coupling devices are provided in FIGS. 10A-F and 11.

Sample Port

Figure 12:
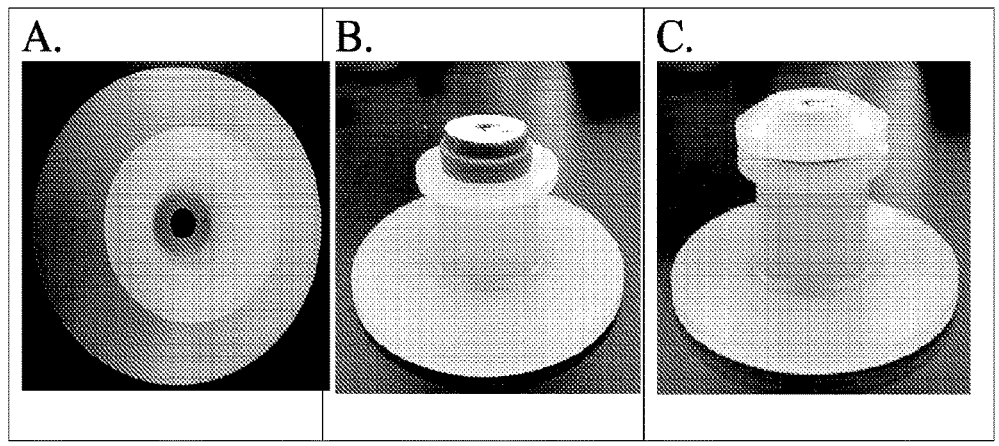
FIG. 12. Exemplary sample port.

In some embodiments, a novel sample port may be incorporated in the DC. FIGS. 12A-C illustrate an exemplary sample port. The disposable sample body is shown in FIG. 12A. The main body may be affixed to a sample port as shown in FIG. 12B. This sampling piece may then be adjoined to a sealing cap as shown in FIG. 12C. The port is typically adjoined to the DC such that the sampling piece and cap are internal to the DC and the opposite side of the port is positioned external to the DC. In one embodiment, then, this disclosure provides a sample port device comprising main body (e.g., a housing) simultaneously in communication with the internal volume and the exterior of a DC. A sampling piece is adjoined to the main body and a capping piece. The sample port may be used to remove samples from the reactants contained within the DC during operation (e.g., at different time points during a reaction).

Improved Impellers

Figure 11:
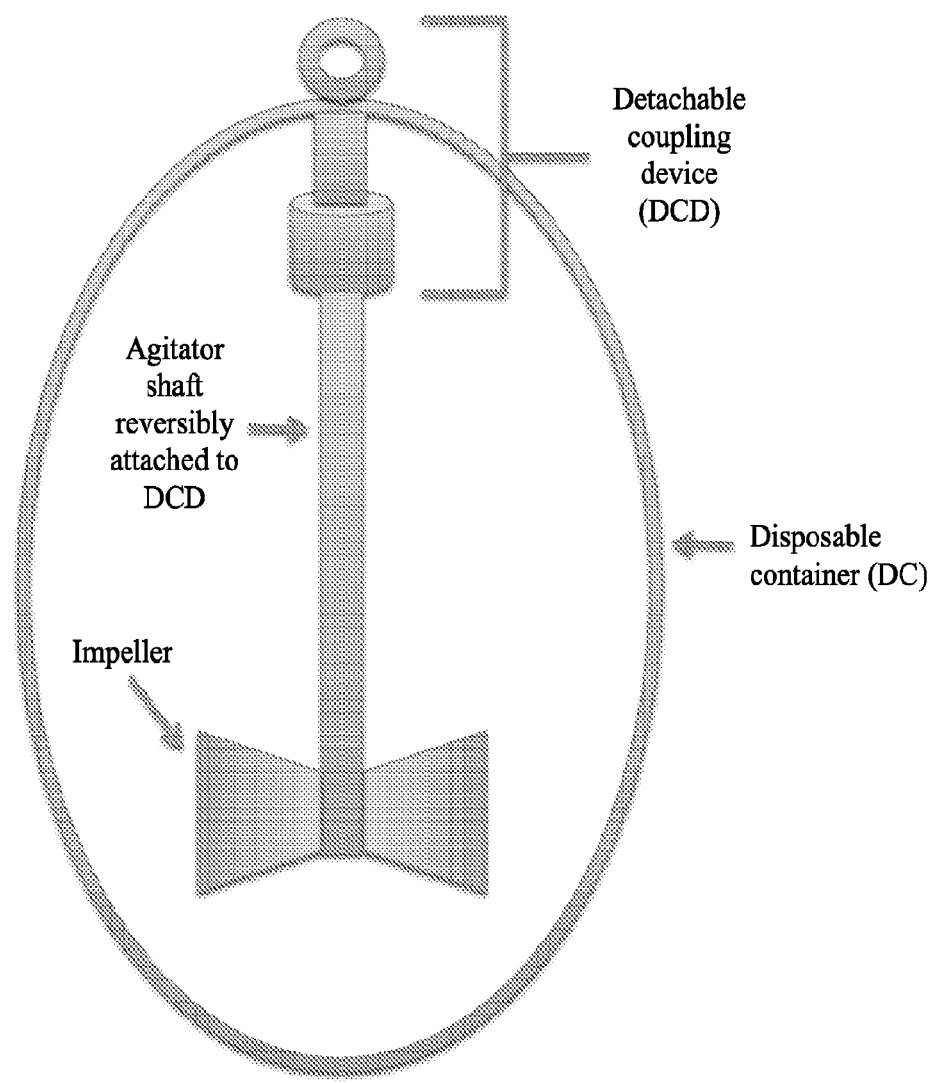
FIG. 11. DCD attached to impeller assembly (agitator shaft and impeller).

This disclosure also provides improved impellers made of lower strength materials (e.g., any of the polymers and/or non-metallic materials described herein) useful in conditions that typically require higher strength materials (e.g., metal). Currently, DCs are limited to mixing systems with low power output as the energy required for mixing he mechanical strength of lower strength materials (e.g. polymeric material such as HDPE). In addition, sterilization procedures (e.g., gamma irradiation) may be incompatible with the use of such lower strength materials. This disclosure provides for impellers made from process-compliant (e.g., sterilizable, disposable, and/or compliant with USP, ISO and/or other biological reactivity standards) materials to be used within DCs. The useful strength of the lower strength materials is increased by providing reinforcement at critical junctures of the impeller as highlighted in FIG. 11, for example. Two exemplary improvements are shown in FIGS. 11B (the expansion of the hub, termed "YoYo") and 11C (the addition of a gusset connecting hub and impeller). Both improvements serve to distribute the forces from the impeller to the hub and averting localization of stress at the hub. This improvement was demonstrated using Finite Element Analysis as described in the Examples Thus, this disclosure provides, in some embodiments, a first container enclosing a sterilizable second container (e.g., a disposable container (DC)), the first container comprising a top surface, a bottom surface, a sterile interior volume, an outlet, and an inlet comprising a sterile filter; the bottom surface comprising a pedestal; the second container being positioned upon the pedestal; wherein: the container constricts the volume of the second container; the filter provides sterility within, and allows gas to enter, the interior volume of the first container; and, the integrity of the second container may be tested measuring the release of gas from the second container through the outlet. Also provided are methods for testing the integrity of such a second container (e.g., DC) by pressurizing the interior volume of the first container to a testing pressure and maintaining the testing pressure for a period of time and measuring any decrease in pressure to detect a defect in the second container.

In some embodiments, this disclosure provides an apparatus comprising a housing comprising an at least partially open panel and a closed panel; a rolled sterile single use container: positioned adjacent to the at least partially open panel of housing; and, comprising inlet and outlet tubing protruding through the open end of the housing, the inlet tubing comprising a sterile filter. Also provided are methods comprising positioning a rolled sterile single use container within a housing comprising a partially open panel and a closed panel, the container being arranged Such that the container to unrolls horizontally from the partially open panel toward the closed panel, the container comprising inlet and outlet tubing arranged opposite the closed end and protruding through the open end, the inlet tubing comprising a sterile filter; and, filling the container with a sterile fluid through the inlet tubing and sterile filter Such that the container unrolls horizontally from the partially open panel toward the closed panel of the housing as the fluid fills the container.

In some embodiments, this disclosure provides an apparatus comprising: a housing comprising an internal volume and an at least partially open bottom panel; a sterile single use container upon the at least partially open bottom panel; inlet and outlet tubing attached to the sterile single use container through the at least partially open bottom panel, the inlet and outlet tubing each comprising a sterile filter, wherein the sterile single use container is filled with sterile fluid through the inlet tubing; and, as the sterile single use container is filled, the volume thereof expands into the internal volume of the housing without application of additional upward force on the sterile single use container. In some embodiments, this disclosure provides methods for filling a sterile single use container using such an apparatus by positioning the sterile single use container within the housing; and, filling the container with a sterile fluid through the inlet tubing and sterile filter Such that the container expands vertically from the partially open panel toward the substantially closed panel of the housing as the fluid fills the container.

In some embodiments, this disclosure provides a foam management device comprising a container comprising an internal volume; tortuous path within the internal volume, the tortuous path being composed of a sterilizable material; the container being attachable to a sterile single use container and a vent to form a passage between the sterile single use container and the vent; wherein the sterile single use container is capable of holding fluid for a reaction that produces gas which is exhausted through passage to reach the vent, the gas optionally comprising liquid in the form of a foam; and, any foam present in the gas is destroyed within the passage Such that only gas reaches the vent. In some embodiments, the tortuous path and the sterile single use container are composed of substantially the same material. In some embodiments, methods for venting gas from a reactor by carrying out a reaction in a sterile single use container affixed to such a device and passing the gas stream resulting from the reaction through the device, wherein any foam present in the gas stream is destroyed prior to reaching the vent are provided.

In some embodiments, this disclosure provides a sterile single use container comprising an internal volume, the container comprising a detachable attachment device comprising a first attachment mechanism substantially positioned within the internal volume of the container; and, a second attachment mechanism substantially positioned on the exterior of the container; wherein the first and second attachment mechanisms may be reversibly attached to one another; the first attachment mechanism further comprises an attachment mechanism for reversibly attaching a device within the internal volume of the container thereto; and, the second attachment mechanism further comprises an attachment mechanism for reversibly attaching a device exterior to the container thereto. In some embodiments, wherein the device exterior to the container is a lifting mechanism. In some embodiments, the device comprises a device body comprising an internal recessed portion and a first surface opposite a second surface; a coupling groove; and, an attachment mechanism; wherein the attachment mechanism is affixed to the first surface and the coupling groove extends from the second surface of the device body formed within the device body and is in communication with the internal recessed portion.

In some embodiments, a device comprising a housing in communication with the internal volume and the exterior of a single use container; comprising one or more attachment points within each of the internal volume and the exterior of the single use container; and, comprising an enclosure comprising a sealing mechanism; wherein a first component may be attached to the housing through an attachment point within the internal volume of the single use container and/or within the sealing mechanism; a second component may be attached to the housing through an attachment point exterior to the single use container and/or within the sealing mechanism; such that the first and second components are reversibly attached to one another.

Figure 13:
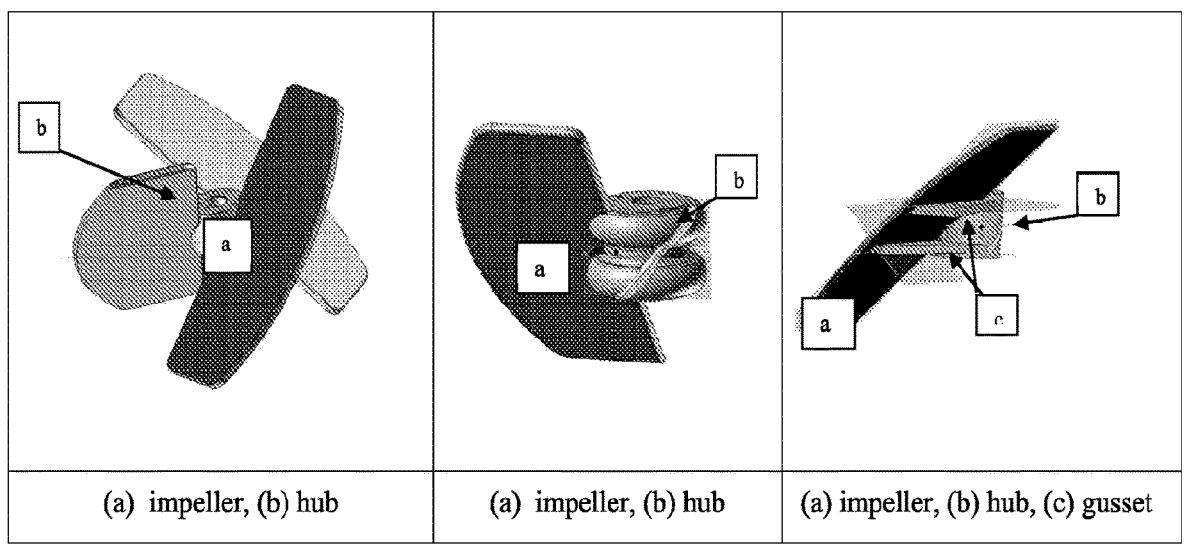
FIG. 13. Exemplary improved impeller.

This disclosure also provides improved impeller designs comprising a rounded double hub as in FIG. 13B or a hub and a gusset as in FIG. 13C.

DCs Having Assymetrically-Positioned Implement Port

DCs are manufactured using film supplied at limited widths, typically requiring the welding panels of film together to produce a DC of sufficient size. Typically, such panels are welded to one another such that the weld or resulting seam is along the central axis of the DC. Implements (e.g., mechanical and other fixtures such as an impeller) are typically attached to the DC by weld fixturing the same to the film along the same central axis. This may present difficulties as the weld and the fixture are positioned along the same axis, which may impair the strength of the weld and/or DC integrity at that point. To solve these problems, the present disclosure provides an asymmetrical bag in which the implement port is moved away from the central axis (e.g., along a second axis). The fixture may then be attached to the DC without crossing the seam (e.g., off the central axis, or axis comprising one or more seams), thereby preserving the integrity of the DC weld and the implement attachment point.

In one embodiment, the DC is constructed from two or more pieces of material (e.g., DC sections) to provide an asymmetrically-positioned implement port (or fixture access point) providing an orifice through which a fixture such as a centrally located fixture may be positioned within the interior of DC. Exemplary implements may include, for instance, implements that are magnetic or mechanically coupled such as an impeller. In certain embodiments, one or more of the DC wall sections are constructed as a single piece of material (e.g., flexible material). Two or more such DC wall section(s) may then be adjoined to one another to form the walls of the DC. For instance, two wall sections may be adjoined to one another along a central axis at which a seam is formed between the sections to form the DC. Where three, four or more wall sections are provided, each of the sections may be adjoined to at least one or two other sections along at least two different axes (e.g., seams) such that the sections collectively form the DC. The implement port may be positioned proximal to an end of one of the sections but distal from the central axis (and/or any other axis comprising a seam) at which the DC wall sections are adjoined to one another (e.g., the seam(s)). A port positioned in this way is referred to herein as an "asymmetrically-positioned implement port". Thus, this asymmetrically-positioned implement port is typically found within one of the wall sections (e.g., a wall subsection) but off of, or away from, a seam at which any two DC wall sections are adjoined to each other. As mentioned above, the asymmetrically-positioned implement port provides an orifice through which the a fixture such as a centrally-located fixture may be positioned within the interior of the DC. The orifice comprises an interior surface and an exterior surface. The interior surface of the orifice is found within the interior chamber of the DC once the DC wall sections are adjoined to one another. The exterior surface of the orifice is found on the exterior of the DC once the DC wall sections are adjoined to one another. The implement may be inserted from the exterior surface of the orifice and past the interior surface of the orifice into the interior chamber of the DC (e.g., such as where an impeller is attached to a shaft, the impeller being ultimately positioned within the DC interior chamber). The implement may alternatively be introduced into the DC interior chamber from the interior surface of the orifice past the exterior of the orifice (e.g., the shaft or a portion thereof may be positioned in the eventual exterior of the DC). Once the DC wall sections are adjoined to one another to form the DC (e.g., surrounding the interior compartment of the DC), the implement is encapsulated within the interior compartment of the DC. In some embodiments, one or more of the DC wall sections may comprise a lifting tab (FIG. 14A-4, part U) that may be used during the adjoining process to lift each section into position such that one section may be adjoined to another section or for another use. One or more of the DC wall sections may comprise one or more ports through which additional implements may be attached to and/or introduced into the DC.

An embodiment of a DC having an assymetrically-positioned fixture access point or implement port is illustrated in FIGS. 14A-C. As shown therein, the DC may be comprised of four DC wall sections (e.g., panels) adjoined to one another to form a common point of attachment. As shown in FIG. 14A-4, each wall section (panel) may include a seam for adjoining each the sections to one another. The sections may be adjoined by any method available to those of ordinary skill in the art (e.g., heat). As shown in the FIG. 14 embodiment, two substantially trapezoid-shaped sections (FIG. 14A-2 ("Tr"), 14B-1, -3) may be adjoined to two substantially kite-shaped sections (FIG. 14A-3 ("K"), 14B-4, -6) such that one end of each substantially kite-shaped section intersects a central end of each substantially trapezoid-shaped sections (FIG. 14A-4). The sections are typically adjoined through the seams (e.g., FIG. 14A-2, represented by space between solid and dashed lines along edges). The two substantially trapezoid-shaped wall sections adjoin one another at the central ends of each (e.g., these central ends being parallel to one another) and intersect the substantially kite-shaped wall sections at a central axis (FIG. 14A-4, dashed line 20). The asymmetrically-positioned fixture access point or implement port (which in this embodiment comprises seal housing A, FIG. 14A-4, 14-C, part 13) is found off of the central axis but near the central end of one of the sections, typically one of the trapezoid-shaped sections. "Near the central end" refers to the positioning of the implement port such that it is not positioned upon, or is positioned away from or off of, the central axis and not on or along a seam. It is this positioning that solves the problems encountered when an implement port is positioned along the central axis comprising a seam (e.g., upon which the trapezoid-shaped sections are adjoined in FIG. 14) such as, for instance, the loss of integrity or weakening of the area of the DC along the seam (e.g., central axis). An implement (e.g., impeller) inserted through the asymmetrically-positioned fixture access point or implement port is shown in FIGS. 14A-1, 14A-2, 14A-3, 14A-4, 14C-1, 14C-3 and 14C-4 (part 12). As also illustrated in FIG. 14, each of the wall sections may comprise one or more hose barbs (e.g., FIG. 14A-3 and A-4, parts B-H and T) that may be used to connect supply and discharge hoses to the DC. One or more wall sections, such as that opposite the wall section including the asymmetrically-positioned implement port, may comprise a drilled tube (sparge, FIGS. 14A-3, 14C-3, and 14C-4, part 14). One or more of the sections may also comprise one or more sets of tube ports (e.g., a series of 2-10 ports through which tubes (FIG. 14A-3, part 7) may be connected to the DC; FIGS. 14A-2 and A-3, part 11; FIG. 14B-1, parts 3, 6, 11; FIG. 14B-3, part 11; FIG. 14B-6, part 5; FIG. 14C-7, parts 4 (inoculum), 5 (drain) and 8-10 (overlay, medium, addition, respectively). A coupling shaft (part 18) and eye-bolt (part 19) may also be included (FIG. 14C-3). Thus, in some embodiments, this disclosure provides a disposable reaction container comprising at least two sheets of material fixably attached to one another along a first axis and at least one fixture access point or implement port along a second axis in at least one of the sheets. In some embodiments, the disposable reaction container comprises multiple (e.g., two, three, four, five, six or more, preferably four) sections adjoined to one another. In preferred embodiments, the sections are adjoined to one another along a seam of at least two other sections to form the container. In certain preferred embodiments, the sections meet along a central axis and the fixture access point or implement port is positioned off of the central axis within one of the sections. Other features of the DC having an assymetrically-positioned implement port are also illustrated by FIG. 14 as would be understood by one of ordinary skill in the art.

In certain embodiments, the DC may be comprised of a flexible (e.g., or semi-flexible), water impermeable material Such as a low-density polyethylene or other polymeric sheets (e.g., between about 0.1-5 mm thickness). The material may be formed of a single-, double- or more layers. The material is typically suitable for maintaining a sterile environment and/or making direct contact with living cells. The material should also be compatible with standard sterilization procedures Such as ionizing radiation. The DC may be formed to provide a compartment size of from about one (1) to about 10,000 liters volume (e.g., any of about one (1), 100, 250, 500, 750, 1000, 1500, 2000, 2500, 3000, 3500, 4000, 4500, 5000, 5500, 6000, 6500, 7000, 7500, 8000, 8500, 9000, 9500 or 10,000 liters). All of the components of the DC (e.g., the container itself, impeller, other mixing components, foam management device, tubes, and the like) may be comprised of the same material (e.g., a low-density polyethylene or other polymeric sheets).

The packaging and integrity testing system may comprise a DC contained in a vessel. The DC and the vessel may be comprised of the same or a different material. For instance, the DC may comprised of a flexible (e.g., or semi-flexible), water impermeable material Such as a low-density polyethylene or other polymeric sheets and the vessel may be comprised of the same or a different material (e.g., stainless steel).

Any of these embodiments may be used alone or with any one or more other embodiments. For instance, a packaging and integrity testing system may comprise a DC appropriate for vertical or horizontal deployment, one or more foam management devices, one or more detachable coupling devices, sample ports and/or improved impellers. Such a system may also include only any of a foam management device, detachable coupling device, sample port and/or improved impeller. One of ordinary skill in the art would understand that various combinations of these embodiments could be used in any other type of system and/or combined into a system, including those not explicitly described herein.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination Such that the description includes both the combination and the absence of the combination (i.e., individual members of the combination). Ranges may be expressed herein as from about one particular value, and/or to about another particular value. When Such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed. All references cited within this disclosure are hereby incorporated into this disclosure by reference in their entirety. Certain embodiments are further described in the following examples. These embodiments are provided as examples only and are not intended to limit the scope of the claims in any way.

EXAMPLES

Example 1. Packaging and Integrity Testing System

Packaging and Integrity test system was demonstrated to pressurize per the apparatus shown in FIGS. 1-5. A one hundred-liter bag (e.g., 8 of FIG. 1) was connected to the inlet port (e.g., 3 of FIG. 1) at the connection at the top of the Packaging/IT System (PAC-IT™) (e.g., 1 of FIG. 1), the one hundred and fifty (150) liter bag was packaged by folding and inserting into a Seventy-five (50) liter PAC-IT™ System (FIGS. 5C-D). Compressed gas was applied to PAC-IT™ at a pressure of 2 psig and no gas was observed leaking from the PAC-IT™. The system was disassembled, and a valve to the DC was cracked to simulate a leak in the bag. Gas pressure was applied and a leak in the film was measured as gas escaping from the bag was captured in an inverted graduated cylinder at a rate of 10-100 mls/min. This demonstrates the ability to package a DC in a manner that provides functionality to be handled in a small package size and to enable verification of container integrity within the packaging.

Integrity Testing System with Vacuum:

A 2000 liter DC was inflated until it expanded to the limits of the container (2000 liter). All connections were then sealed and the DC was left for 16 hours. The Unit was then observed and the DC had partially collapsed by approximately 50 liters (e.g. a leak rate of approx. 50 mls/min). One liter of water was added to the tank bottom a vacuum was pulled on the DC. A stream of bubbles of approx 50-100 mls/mn were observed within the DC at a seam welded to the seal housing flange. This demonstrated that the V-Test™ with water over the defect was effective at locating the defect by visual observation.

Example 2. Vertical Deployment System

The vertical deployment was demonstrated at a 3,000 liter scale (FIG. 6). The DC was first configured in packaging with all ports pinched closed and tubing assemblies folded keeping the top assemblies at the top of the DC. The DC was then loaded into the container. The DC was then connected to a compressed gas source. Compressed air/gas was then introduced to the DC with the valve to the vent filter in the closed position. The DC was filled until it was observed that all creases in the bag were removed and the top of the DC. The DC inflated successfully in the vessel with the tube assemblies maintaining their positions as originally packaged and loaded. The top assemblies were then disconnected and laid back on the top of the DC, and the valve to the vent filter was then opened to deflate the DC and remove from the Container. The DC successfully collapsed into the base of the container for removal this demonstrated the benefit as compared to traditional means of deployment that include the mechanical external expanding of the DC into the container.

Example 3. Horizontal Deployment System

The Horizontal Deployment System (FIG. 7) was demonstrated at a 3,000 liter scale wherein the DC was first configured as it would be in packaging (e.g., the top of the DC was rolled back toward the bottom of the DC). The DC was then be removed from the packaging and laid to deploy horizontally. The DC was filled with fluid from the base of the DC and the DC unrolled and deployed (unrolled horizontally as shown in FIGS. 7A and 7C). This demonstrated the ease in which a bag can be prepackaged to maintain a compact packing volume and expand without additional handling.

Example 4. Detachable Coupling Devices

Figure 10C:
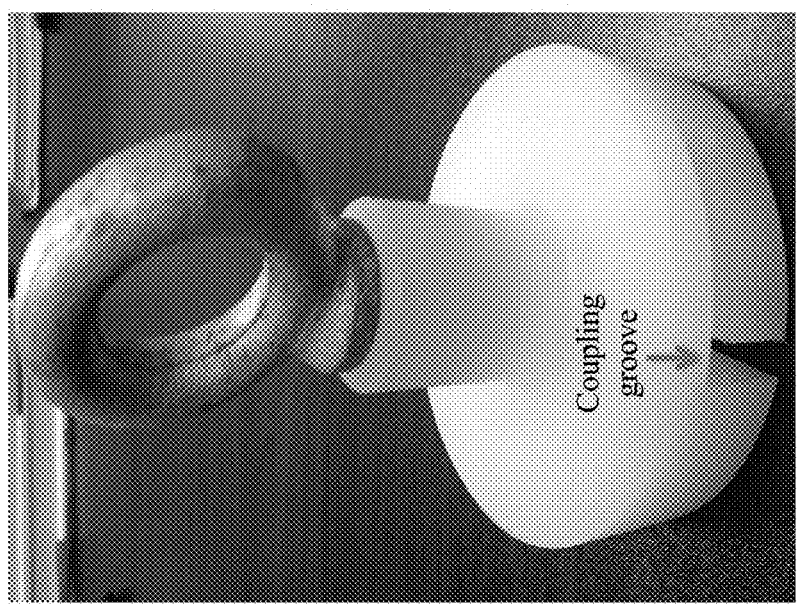
FIG. 10. Exemplary detachable coupling device (DCD). A. Top and isometric view. B. Side view. C. Second isometric view. D. DCD attached to DC. E. DC being manipulated using DCD. F. DC with DCD in container.
Figure 10B:
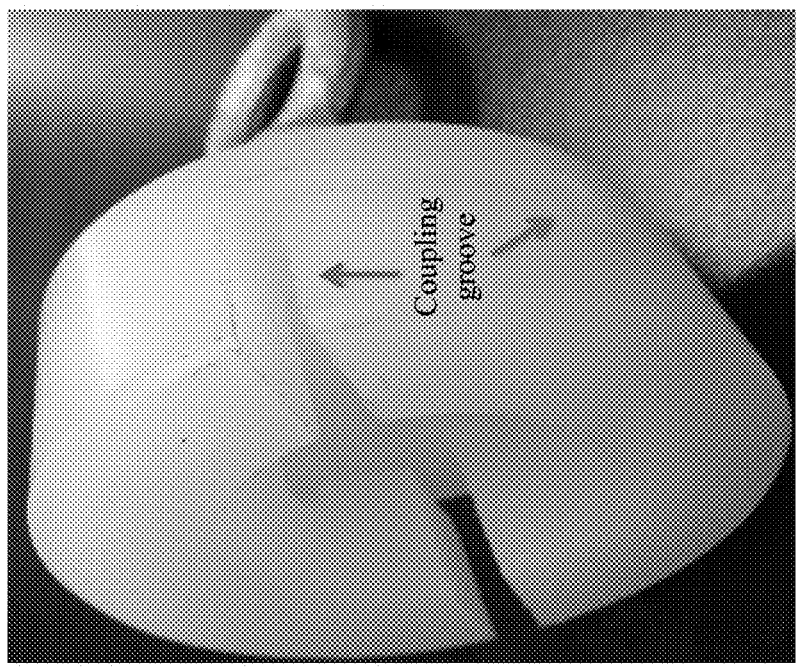
Figure 10D:
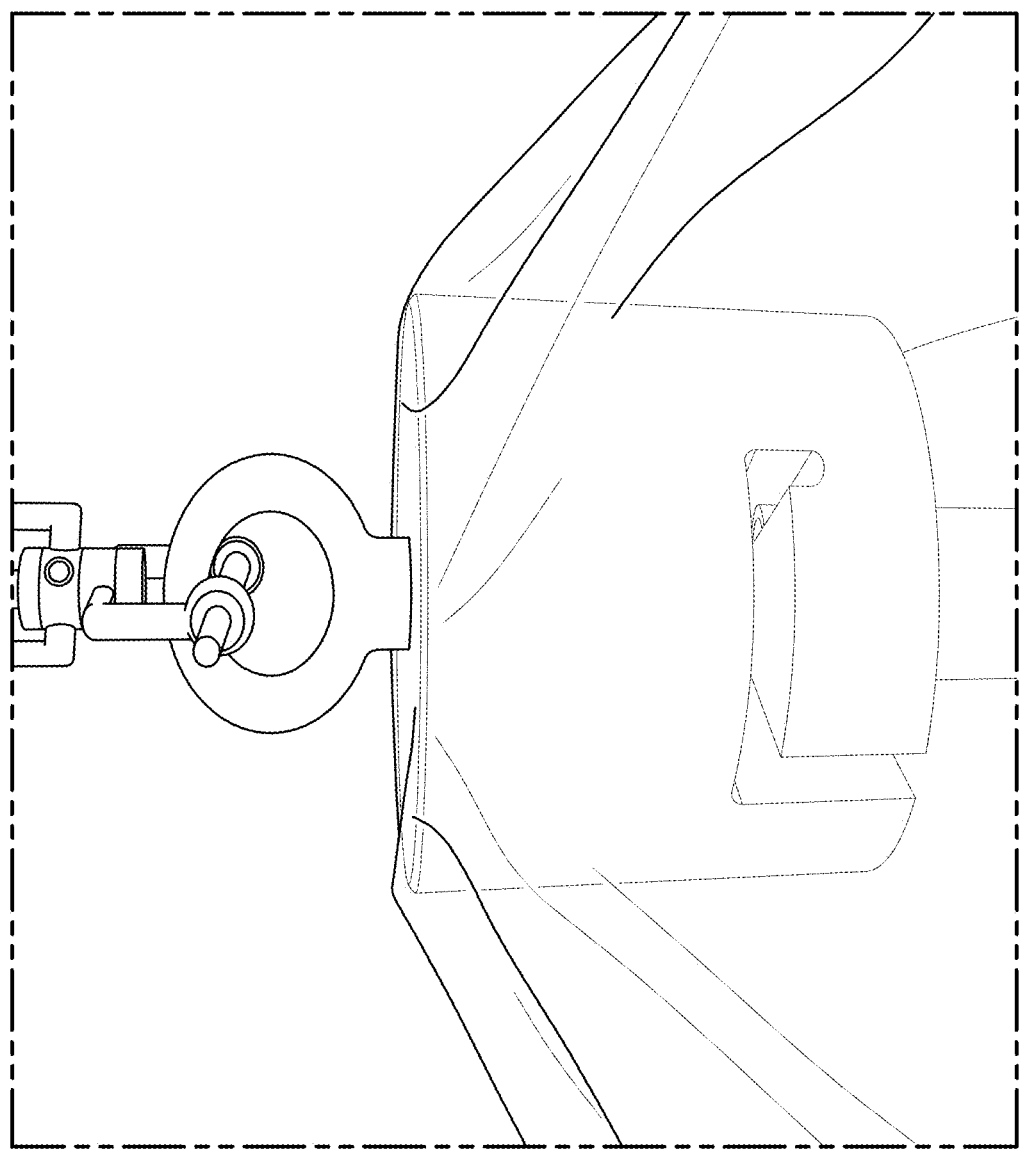
Figure 10E:
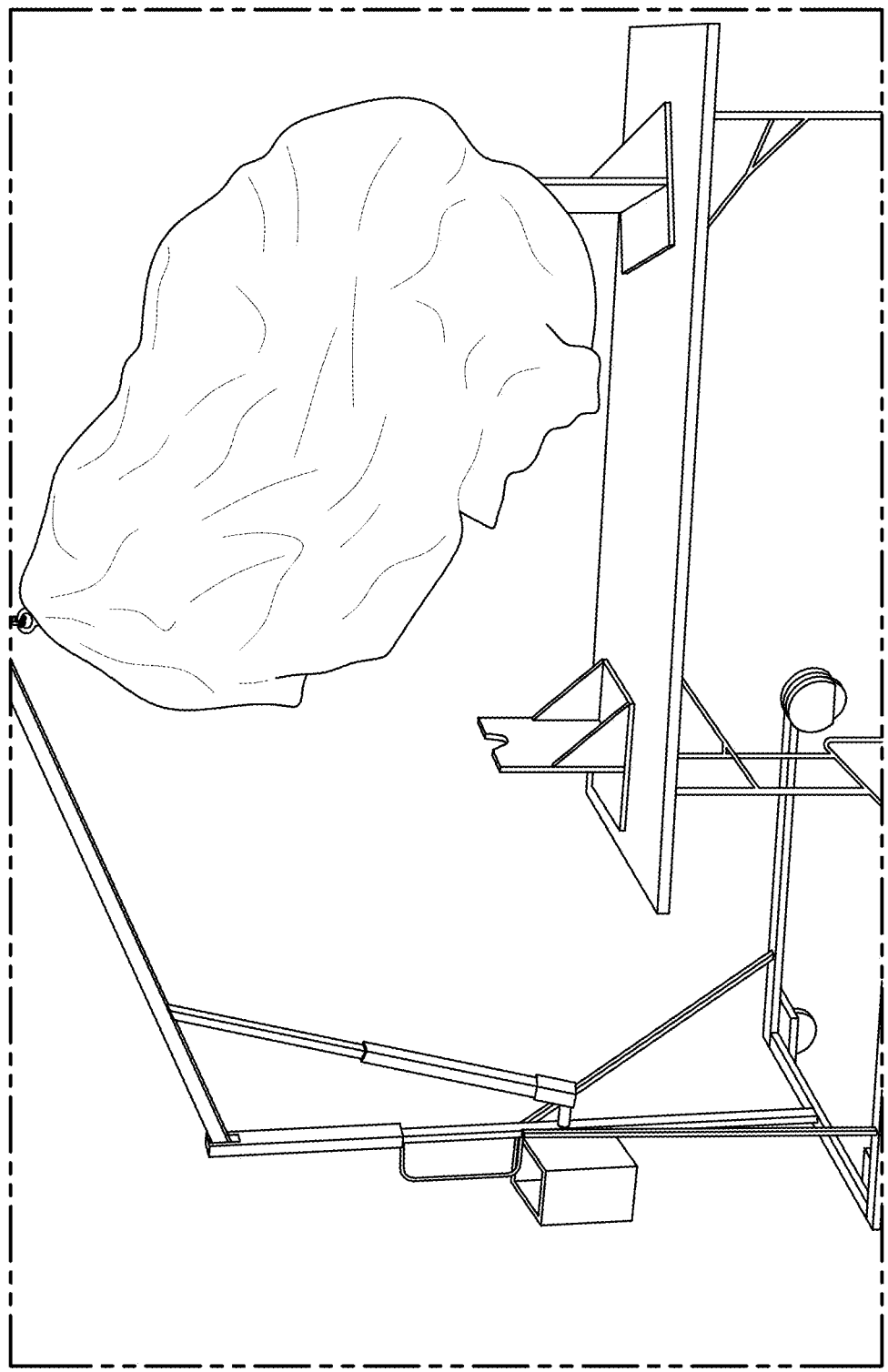
Figure 10F:

The Detachable Coupling Device (DCD) was demonstrated at a scale of to handle 70 pounds weight and dimension 50"×18"×18". It was designed, constructed and successfully integrated with the DC. FIG. 10D shows the DCD welded and integrated with the DC. FIG. 11B shows the DCD being used to lift and transport the DC to its container. FIG. 10F shows the DCD loaded in the container. The DCD therefore met the requirements enabling the handling of of large apparatus (e.g. agitator shaft and impellers or other assemblies which may be integrated as a part of a DC as shown in FIG. 11) within a DC Example 5. Improved Impellers Improved performance provided by the improved impeller designs (FIGS. 13B and 13C) was demonstrated by both Finite Element Analysis (FEA) and by Physical Testing by comparing a traditional low shear impeller (FIG. 13A) and the disclosed novel designs (FIGS. 13B and 13C). Tables 1 and 2 present data relating to a design incorporating two High Density Polyethylene (HDPE) 18" Low shear impellers. Maximum principle stress (psi) was also shown (by FEA) to be improved by a factor of about two for the Yo Yo design (FIG. 13B) and by a factor of about three for the Gusset design (FIG. 13C). This data demonstrates the increase in strength provided by the Yo Yo and Gusset designs, likely by redistribution and reduction in localized stress. Physical testing was performed using a time study performed with the impellers at a rate of 100 RPM in a 3,000 liter vessel of water until the impellers reached an acceptable lifetime, which was determined to be 60 days. The results presented in Table 2 show that the traditional impellers broke after 47 days, below the acceptance criteria and the improved impellers had exceeded the acceptance criteria.

TABLE 1

| Impeller Design | Design Change Description | Maximum Principle Stress (psi) |
|---|---|---|
| Baseline | None | 1403 |
| YoYo | Expanded the hub radially and axially. Created two additional points of stress spreading out the maximum load. | 776 |
| Gusset | Hub expanded both radially and axially in a different fashion than in modifications 1 and 2 with two gussets placed on the trailing edge of the blade. | 473 |

TABLE 2

| Impeller Design | Design Change Description | Days to Failure |
|---|---|---|
| Baseline | None | 47 |
| YoYo | Expanded the hub radially and axially. Created two additional points of stress spreading out the maximum load. | |
| Gusset | Hub expanded both radially and axially in a different fashion than in modifications 1 and 2 with two gussets placed on the trailing edge of the blade. | >150 |

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A single use disposable container comprising:
    an internal volume and an attachment device;
    the attachment device comprising:
        a first attachment mechanism comprising a device body positioned within the internal volume of the container,
        the device body comprising: a first surface opposite a second surface; an internal recessed portion; and, a coupling groove in communication with the internal recessed portion, the coupling groove comprising a first portion extending from the second surface of the device body toward the first surface and a second portion continuous with the first portion and extending parallel to said second surface; and,
        a second attachment mechanism extending from the first surface of the first attachment mechanism and external to the internal volume of the single use disposable container.

2. The single use disposable container of claim 1 wherein the second attachment mechanism is reversibly attached to a lifting device.

3. The single use disposable container of claim 2 wherein the second attachment mechanism device comprises an eye bolt.

4. The single use disposable container of claim 3 wherein the single use disposable container is a film and wherein a portion of said film is sealed to the first surface of the attachment device.

5. The single use disposable container of claim 2 wherein the single use disposable container is a film and wherein a portion of said film is sealed to the first surface of the attachment device.

6. The single use disposable container of claim 1 wherein the single use disposable container is a film and wherein a portion of said film is sealed to the first surface of the attachment device.

* * * * *